US009448120B2

(12) United States Patent
Huang

(10) Patent No.: US 9,448,120 B2
(45) Date of Patent: Sep. 20, 2016

(54) METHOD FOR ADJUSTING COMPENSATING OPTICAL SYSTEM AND COMPENSATING OPTICAL SYSTEM

(71) Applicant: HAMAMATSU PHOTONICS K.K., Hamamatsu-shi, Shizuoka (JP)

(72) Inventor: Hongxin Huang, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 108 days.

(21) Appl. No.: 14/404,997

(22) PCT Filed: Apr. 1, 2013

(86) PCT No.: PCT/JP2013/059958
§ 371 (c)(1),
(2) Date: Dec. 2, 2014

(87) PCT Pub. No.: WO2013/183341
PCT Pub. Date: Dec. 12, 2013

(65) Prior Publication Data
US 2015/0146196 A1    May 28, 2015

(30) Foreign Application Priority Data
Jun. 4, 2012  (JP) ................................. 2012-127222

(51) Int. Cl.
G01J 9/00   (2006.01)
G01M 11/02  (2006.01)
(Continued)

(52) U.S. Cl.
CPC .. *G01J 9/00* (2013.01); *A61B 3/14* (2013.01); *G01M 11/0257* (2013.01); *G02F 1/1313* (2013.01); *G02F 2203/18* (2013.01); *G02F 2203/50* (2013.01)

(58) Field of Classification Search
CPC ....... G01J 9/00; G01M 11/0257; A61B 3/14; G02F 1/1313; G02F 2203/50

USPC ............ 356/212, 214, 214.5, 457, 346, 479, 356/491; 351/211, 159; 250/201.9, 237 R
See application file for complete search history.

(56) References Cited

U.S. PATENT DOCUMENTS 6,570,143 B1 *  5/2003  Neil .......................... G01J 9/00
                                                    250/201.9
6,717,104 B2 *  4/2004  Thompson, Jr. ...... B23K 26/032
                                                    219/121.73

(Continued)

FOREIGN PATENT DOCUMENTS

JP    2005-292662 A    10/2005
JP    2008-519298 A     6/2008
JP    2009-192832 A     8/2009

OTHER PUBLICATIONS

Hongxin Huang et al., "Adaptive aberration compensation system using a high-resolution liquid crystal on silicon spatial light phase modulator," Proceedings of SPIE, 2008, pp. 71560F-1-71560F-10, vol. 7156.

(Continued)

Primary Examiner — Sang Nguyen
(74) Attorney, Agent, or Firm — Drinker Biddle & Reath LLP

(57) ABSTRACT

A positional deviation between a phase distribution in a wavefront sensor and a compensation phase pattern in a wavefront modulator is corrected in a short time and with high accuracy by a method including a first step of causing the wavefront modulator to display a singularity generation pattern, a second step of measuring in the sensor an adjustment wavefront shape when an optical image modulated by the singularity generation pattern enters the wavefront sensor, a third step of detecting a position of a singularity in the adjustment wavefront shape from a measurement result in the sensor, and a fourth step of adjusting a positional deviation between a wavefront shape measured in the wavefront sensor and a compensation pattern displayed on the wavefront modulator based on a positional deviation of the position of the singularity.

10 Claims, 28 Drawing Sheets

(51) Int. Cl.
*A61B 3/14* (2006.01)
*G02F 1/13* (2006.01)

(56) References Cited

U.S. PATENT DOCUMENTS

| | | | | |
|---|---|---|---|---|
| 7,095,556 | B2* | 8/2006 | Iketaki | G02B 26/08 250/458.1 |
| 7,639,369 | B2* | 12/2009 | Owner-Petersen | G01J 9/00 351/211 |
| 8,120,765 | B2* | 2/2012 | Huang | A61B 3/1015 250/201.9 |
| 2002/0180931 | A1* | 12/2002 | Dick | A61B 3/14 351/211 |
| 2003/0062464 | A1* | 4/2003 | Byren | G02B 26/06 250/201.9 |
| 2005/0105044 | A1* | 5/2005 | Warden | A61B 3/1015 351/159.08 |
| 2006/0175528 | A1* | 8/2006 | Greenaway | G01J 9/00 250/201.9 |
| 2011/0096293 | A1* | 4/2011 | Hirose | A61B 3/102 351/206 |
| 2011/0122416 | A1* | 5/2011 | Yang | A61B 5/0059 356/457 |

OTHER PUBLICATIONS

Abdul Awwal et al., "Characterization and Operation of a Liquid Crystal Adaptive Optics Phoropter," Proceedings of SPIE, 2003, pp. 104-122, vol. 5169.

Chenxi Huang et al., "Correlation matching method for high-precision position detection of optical vortex using Shack-Hartmann wavefront sensor," Optics Express, Nov. 19, 2012, pp. 26099-26109, vol. 20, No. 24.

Mingzhou Chen et al., "Detection of phase singularities with a Shack-Hartmann wavefront sensor," Optical Society of America, Jul. 7, 2007, pp. 1994-2002, vol. 24, No. 7.

English-language translation of International Preliminary Report on Patentability (IPRP) dated Dec. 18, 2014 that issued in WO Patent Application No. PCT/JP2013/059958.

* cited by examiner

Fig.16
(a)
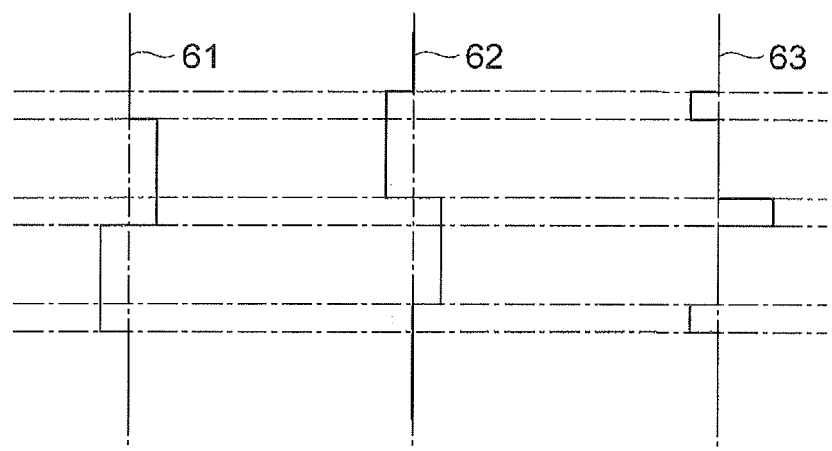
(b)
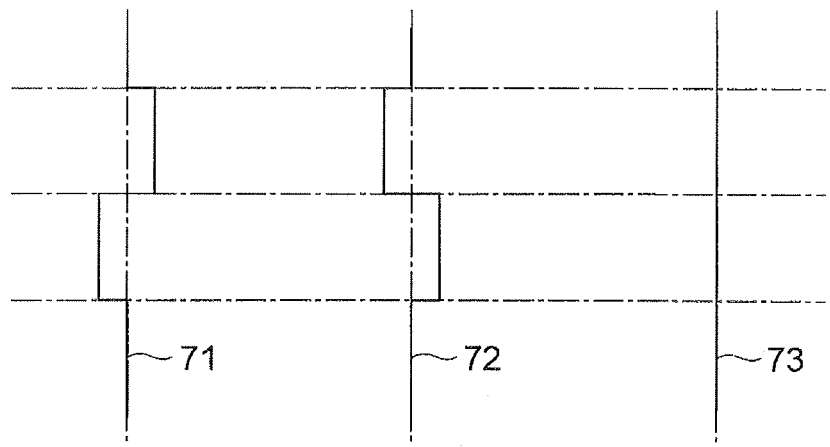

METHOD FOR ADJUSTING COMPENSATING OPTICAL SYSTEM AND COMPENSATING OPTICAL SYSTEM

TECHNICAL FIELD

The present invention relates to a method for adjusting an adaptive optics system and an adaptive optics system.

BACKGROUND ART

Non-Patent Document 1 describes a method for adjusting an adaptive optics system by a phase measurement method. The phase measurement method is a method of causing a wavefront modulator to display a known phase distribution, and then measuring the phase distribution by a wavefront sensor, and contrasting the measurement result with the known phase distribution to thereby make coordinates on a modulation plane and coordinates on a detection plane correspond to each other.

CITATION LIST

Non Patent Literature

Non-Patent Document 1: Abdul Awwal et al., "Characterization and Operation of a Liquid Crystal Adaptive Optics Phoropter", Proceedings of SPIE, Volume 5169, pp 104-122 (2003)

SUMMARY OF INVENTION

Technical Problem

The adaptive optics technology is a technology for dynamically removing aberration by measuring optical aberration (a wavefront distortion) using a wavefront sensor and controlling a wavefront modulator based on the measurement result. This adaptive optics technology allows improving imaging characteristics, the degree of condensation, the image S/N ratio, and the measurement accuracy. Conventionally, the adaptive optics technology has been used mainly for astronomical telescopes and large-sized laser equipment. Recently, adaptive optics technology has begun to be applied also to fundus cameras, scanning laser ophthalmoscopes, optical coherence tomography, laser microscopes, and the like. Such imaging using the adaptive optics technology enables observation at non-conventional high resolution. For example, by applying the adaptive optics technology to a fundus imaging device to observe the back of the eye (fundus oculi), aberration due to the eyeball is removed, and microstructures at the fundus oculi such as, for example, visual cells, nerve fibers, and capillaries can be clearly depicted. Use for early diagnosis of circulatory diseases as well as ophthalmic diseases can be expected.

An adaptive optics system for realizing the adaptive optics technology as above is composed mainly of a wavefront modulator, a wavefront sensor, and a control device for controlling these. Moreover, for making the adaptive optics system operate properly to eliminate a wavefront distortion completely, adjustment (calibration) of the adaptive optics system is required. The calibration of the adaptive optics system is mainly to adjust corresponding relationships of a control signal to the wavefront modulator and a measurement signal by the wavefront sensor.

The corresponding relationships are roughly divided into the following two types.

(1) Corresponding relationship of the magnitude of a control signal to the wavefront modulator and the magnitude of a measurement signal by the wavefront sensor.

(2) Corresponding relationship of the position of a control point in the wavefront modulator and the position of a measurement point in the wavefront sensor.

The corresponding relationship of the above (1) can be easily obtained from phase modulation characteristics of the wavefront modulator. In addition, the phase modulation characteristics of the wavefront modulator also sometimes depend on the environment (e.g., temperature and temporal change) in which the wavefront modulator is being used, but this is at a negligible level in most cases. Also, the corresponding relationship of the above (2) depends on the spatial position relationship of the wavefront modulator and wavefront sensor (position relationship mainly within a plane that intersects the optical axis).

In the adaptive optics system, the wavefront is controlled at an accuracy of the wavelength of light or below (e.g., a submicron level). Hence, due to vibration during transportation or at the installation site or deformation or the like by heat of a member that holds the wavefront sensor or wavefront modulator, a positional deviation may occur between a phase distribution that is measured in the wavefront sensor and a phase pattern for compensation that is displayed on the wavefront modulator. Thus, adjustment work regarding the above (2) is desirably performed not only in assembly and maintenance of an apparatus including the adaptive optics system but also immediately before using the apparatus and in between a plurality of times of imaging. Therefore, means for executing the adjustment work described above easily and with high accuracy is required.

However, in the phase measurement method described in Non-Patent Document 1, because it is necessary to calculate a phase distribution from the measurement result of the wavefront sensor, the accuracy of adjustment depends on the phase modulation accuracy of the wavefront modulator, the phase measurement accuracy of the wavefront sensor, and the accuracy of an optical image for calibration, and it is difficult to stably realize a high accuracy.

Also, as a method for adjusting an adaptive optics system, an influence matrix method is also known conventionally. In the influence matrix method, a deformable mirror and a Shack-Hartmann type wavefront sensor are used. That is, voltage for adjustment is applied in order to a plurality of actuators contained in the deformable mirror, and changes in a measurement signal from the wavefront sensor due to changes in the wavefront caused by the voltage application are recorded. As a result, a response matrix of a measurement signal corresponding to a voltage applied to the deformable mirror is constructed. This matrix is the influence matrix. Moreover, an inverse matrix of the influence matrix serves as a control matrix, and this control matrix is used to perform adjustment of the adaptive optics system. However, in the influence matrix method, a large number of pixels of the wavefront modulator involve a huge amount of computation, which requires a long time for adjustment work.

The present invention has been made in view of these problems, and an object thereof is to provide a method for adjusting an adaptive optics system and an adaptive optics system capable of correcting a positional deviation between a phase distribution that is measured in the wavefront sensor and a compensation phase pattern that is displayed on the wavefront modulator in a short time and with high accuracy.

Solution to Problem

In order to solve the above-described problems, a method for adjusting an adaptive optics system according to the present invention is a method for adjusting an adaptive optics system which includes a wavefront modulator receiving an optical image from a light source or an observation object, and a wavefront sensor receiving an optical image from the wavefront modulator to measure a wavefront shape of the optical image, and compensates for a wavefront distortion by controlling a pattern to be displayed on the wavefront modulator based on the wavefront shape measured by the wavefront sensor, and includes a first step of causing the wavefront modulator to display a singularity generation pattern which is a pattern including a phase singularity (hereinafter, "phase singularity" is abbreviated as "singularity") at a predetermined position, a second step of measuring in the wavefront sensor an adjustment wavefront shape which is a wavefront shape when an optical image modulated by the singularity generation pattern enters the wavefront sensor, a third step of detecting a position of the singularity in the adjustment wavefront shape from a measurement result in the wavefront sensor, and a fourth step of adjusting a positional deviation between a wavefront shape measured in the wavefront sensor and a compensation pattern displayed on the wavefront modulator based on a positional deviation of the position of the singularity detected in the third step with respect to the predetermined position.

Also, an adaptive optics system according to the present invention includes a wavefront modulator receiving an optical image from a light source or an observation object, a wavefront sensor receiving an optical image from the wavefront modulator to measure a wavefront shape of the optical image, and a control section compensating for a wavefront distortion by controlling a pattern to be displayed on the wavefront modulator based on the wavefront shape measured by the wavefront sensor, and in the system, the control section includes a singularity generation pattern preparing section causing the wavefront modulator to display a singularity generation pattern which is a pattern including a singularity at a predetermined position, and a singularity detecting section detecting a position of the singularity in an adjustment wavefront shape which is a wavefront shape when an optical image modulated by the singularity generation pattern enters the wavefront sensor, based on a measurement result in the wavefront sensor, and the control section adjusts a positional deviation between a wavefront shape measured in the wavefront sensor and a compensation pattern displayed on the wavefront modulator based on a positional deviation of the position of the singularity detected by the singularity detecting section with respect to the predetermined position.

Advantageous Effects of Invention

By a method for adjusting an adaptive optics system and an adaptive optics system according to the present invention, a positional deviation between a phase distribution measured in the wavefront sensor and a compensation phase pattern displayed on the wavefront modulator can be corrected in a short time and with high accuracy.

BRIEF DESCRIPTION OF DRAWINGS

FIG. 16 includes views explaining advantages of that the accuracy of adjustment (calibration) of the adaptive optics system is high.

DESCRIPTION OF EMBODIMENTS

Hereinafter, an embodiment of a method for adjusting an adaptive optics system and an adaptive optics system according to the present invention will be described in detail with reference to the accompanying drawings. In the description of the drawings, the same components will be denoted by the same reference symbols, and overlapping description will be omitted.

Embodiment

Figure 1:
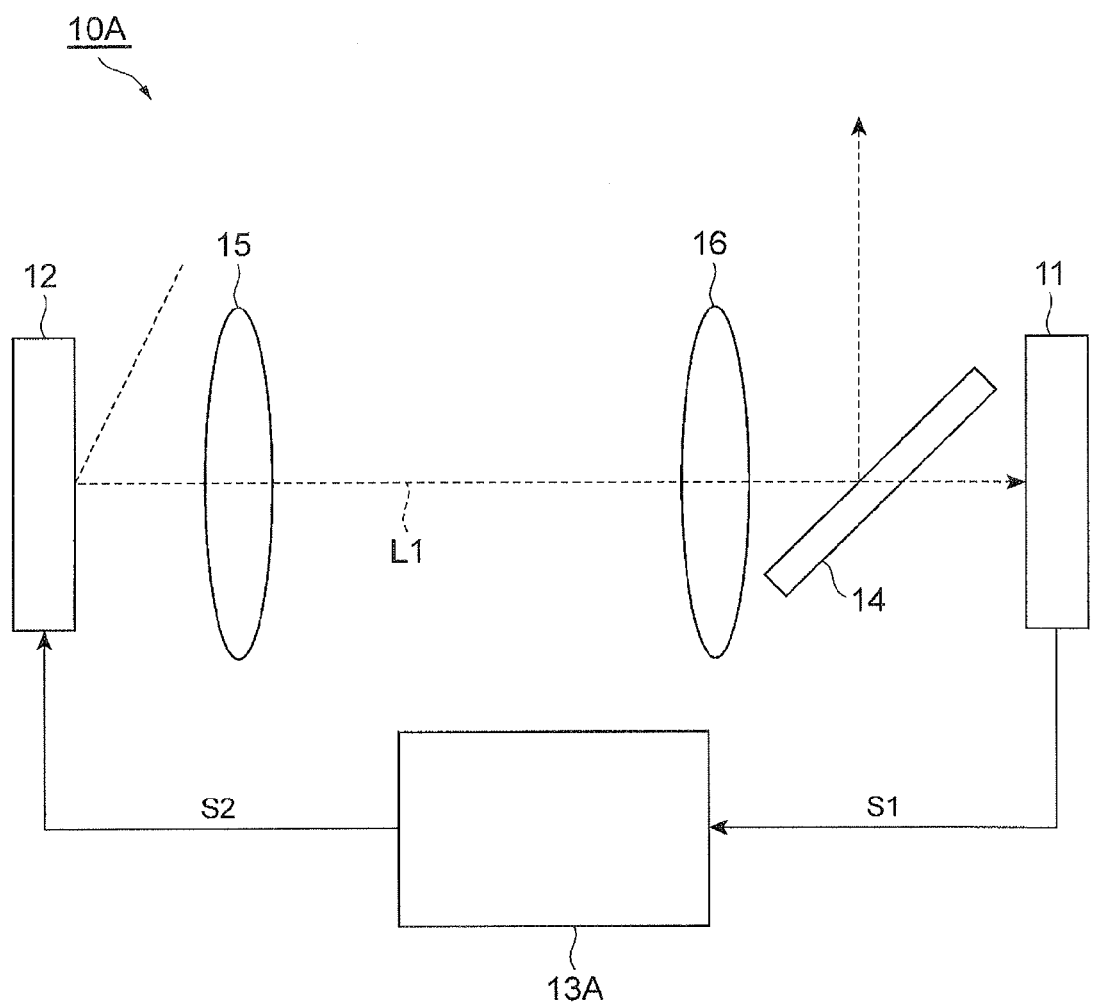
FIG. 1 is a view showing an overview of an adaptive optics system according to an embodiment.

FIG. 1 is a view showing an overview of an adaptive optics system 10A according to the present embodiment. The adaptive optics system 10A is incorporated in, for example, an ophthalmologic examination apparatus, a laser processing apparatus, a microscope apparatus, or an adaptive optics apparatus.

The adaptive optics system 10A includes a wavefront sensor 11, a wavefront modulator 12, a control section 13A, a beam splitter 14, and relay lenses 15 and 16. The wavefront sensor 11 measures a wavefront shape (typically, expressed by aberration of an optical system, and representing distortion of the wavefront, that is, a deviation of the wavefront from a reference wavefront) of an optical image L1 that has arrived from the wavefront modulator 12, and provides a measurement signal S1 indicating the measurement result to the control section 13A. The wavefront modulator 12 is an element that controls the wavefront of the optical image L1, and is composed of, for example, a spatial light modulator (SLM). The control section 13A, based on the measurement signal S1 obtained from the wavefront sensor 11, generates a control signal S2 for providing an appropriate pattern to the wavefront modulator 12.

The beam splitter 14 is arranged between the wavefront sensor 11 and the wavefront modulator 12, and splits the optical image L1. The beam splitter 14 may be any of a polarization direction independent type, a polarization direction dependent type, or a wavelength dependent type (dichroic mirror). The optical image L1 split by the beam splitter 14 is sent to a photodetector such as, for example, a CCD, a photomultiplier tube, or an avalanche photodiode. This photodetector has been incorporated in, for example, a scanning laser ophthalmoscope (SLO), optical coherence tomography (OCT), a fundus camera, a microscope, a telescope, or the like. The relay lenses 15 and 16 are arranged aligned in the optical axis direction between the wavefront sensor 11 and the wavefront modulator 12. By these relay lenses 15 and 16, the wavefront sensor 11 and the wavefront modulator 12 are maintained in an optically conjugate relationship with each other. In addition, between the wavefront sensor 11 and the wavefront modulator 12, an optical imaging lens and/or a deflecting mirror, etc., may be further arranged.

Figure 2:
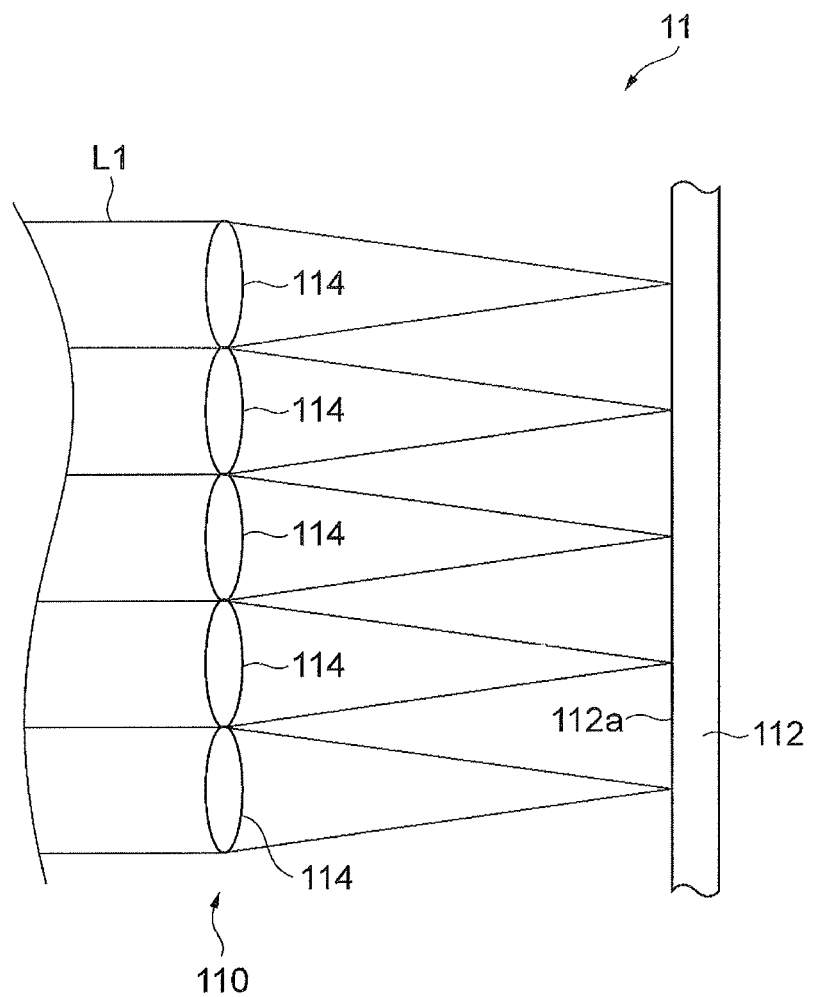
FIG. 2 is a sectional view schematically showing a configuration of a wavefront sensor, and shows a section taken along the optical axis of an optical image.

FIG. 2 is a sectional view schematically showing a configuration of the wavefront sensor 11 of the present embodiment, and shows a section taken along the optical axis of the optical image L1. The wavefront sensor 11 can be either an interference type or a non-interference type, and in the present embodiment, a non-interference type of Shack-Hartmann type wavefront sensor having a lens array 110 and an image sensor 112 is used as the wavefront sensor 11. When such a non-interference type wavefront sensor 11 is used, vibration resistance is excellent as compared with when an interference type wavefront sensor 11 is used, and there is an advantage that configuring a wavefront sensor and arithmetic processing of measurement data can be simply performed.

The image sensor 112 has a light receiving surface 112a at a position to overlap back focal planes of a plurality of lenses 114 composing the lens array 110, and detects an intensity distribution of condensed light images by the lenses 114. Because the magnitude of a deviation between the position of a condensed light image by the lens 114 and a reference position is proportional to a local wavefront tilt of the optical image L1 entering the lens 114, by detecting the magnitude of a deviation of the condensed light image position from the reference position for each lens 114, a distribution of phase gradients of an incoming wavefront can be easily obtained.

Here, as the reference position to be used for calculating the magnitude of a deviation of the condensed light image position, a position where the optical axis of each of the plurality of lenses 114 and the light receiving surface 112a of the image sensor 112 intersect is preferred. This position is easily determined by a centroid calculation, using a condensed light image obtained by making a parallel plane wave normally incident onto each lens 114.

Figure 3:
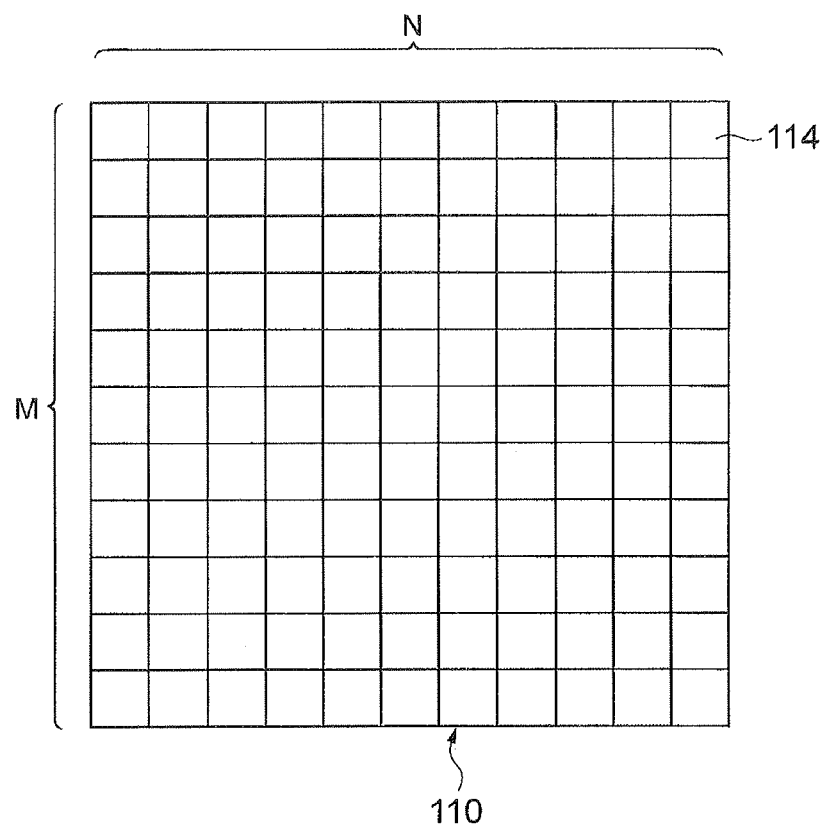
FIG. 3 is a view of a lens array of the wavefront sensor from the optical axis direction of the optical image.

FIG. 3 is a view of the lens array 110 from the optical axis direction of the optical image L1 As shown in FIG. 3, the plurality of lenses 114 of the lens array 110 are arranged in, for example, a two-dimensional grid pattern of M rows and N columns (N and M are integers not less than 2). In addition, respective pixels composing the light receiving surface 112a of the image sensor 112 are also arranged in a two-dimensional grid pattern, and its horizontal direction and vertical direction are coincident with the horizontal direction and vertical direction of the lens array 110, respectively. However, the pixel pitch of the image sensor 112 is sufficiently smaller than the pitch of the lenses 114 in the lens array 110 (e.g., the aperture size of the lens 114) so as to allow detecting the magnitude of a deviation of the condensed light image position from the reference position at high accuracy.

The wavefront modulator 12 is an element receiving an optical image L1 from a light source or observation object, and modulates the wavefront of the optical image L1 for output. Specifically, the wavefront modulator 12 has a plurality of pixels (control points) arrayed in a two-dimensional grid pattern, and changes the modulation amount (e.g., the phase modulation amount) of the respective pixels according to a control signal S2 input from the control section 13A. In addition, the wavefront modulator 12 is also called a spatial light modulator (SLM). Examples of the wavefront modulator 12 include an LCOS (Liquid Crystal On Silicon) type spatial light modulator, an electrically addressable spatial light modulator in which a liquid crystal display element and an optically addressable liquid crystal spatial light modulator are coupled, and a micro electro mechanical systems (MEMS) device. In addition, FIG. 1 shows a reflection type wavefront modulator 12, but the wavefront modulator 12 may be a transmission type.

Figure 4:
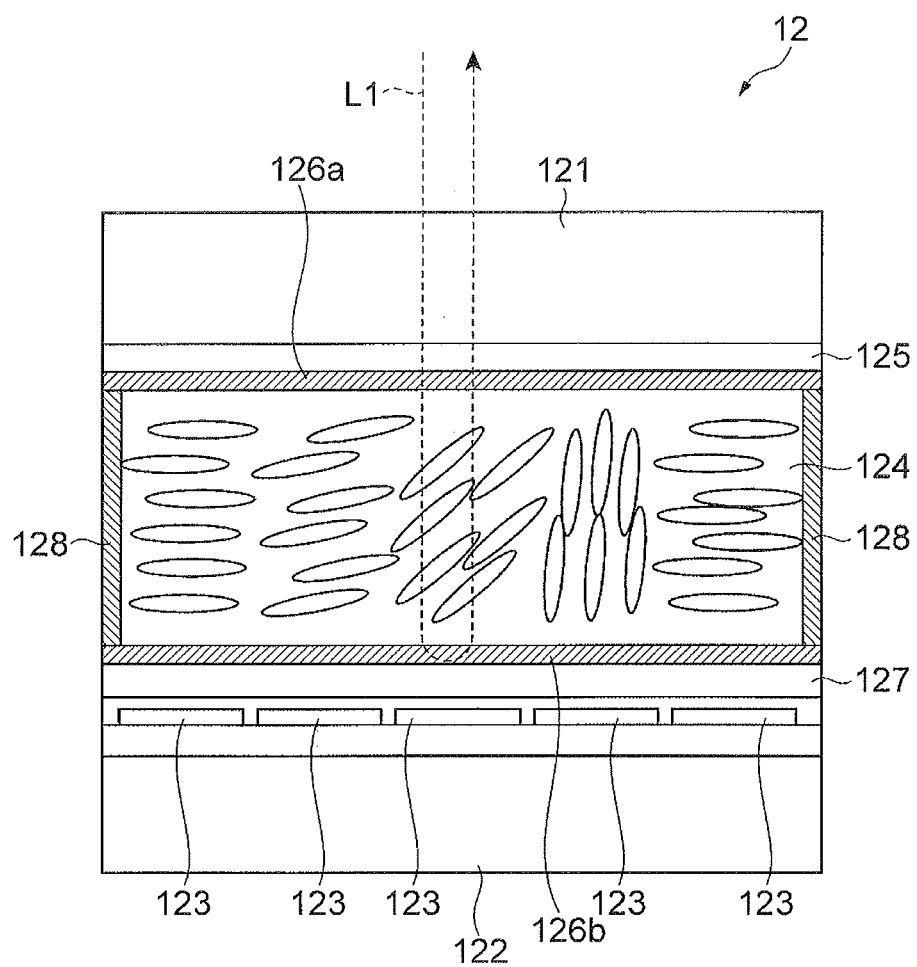
FIG. 4 is a sectional view schematically showing an LCOS type wavefront modulator as an example of a wavefront modulator, and shows a section taken along the optical axis of an optical image.

FIG. 4 is a sectional view schematically showing an LCOS type wavefront modulator as an example of the wavefront modulator 12 of the present embodiment, and shows a section taken along the optical axis of the optical image L1. The wavefront modulator 12 includes a transparent substrate 121, a silicon substrate 122, a plurality of pixel electrodes 123, a liquid crystal portion (modulation portion) 124, a transparent electrode 125, orientation films 126a and 126b, a dielectric mirror 127, and a spacer 128. The transparent substrate 121 is made of a material that transmits the optical image L1, and arranged along a principal surface of the silicon substrate 122. The plurality of pixel electrodes 123 are arrayed in a two-dimensional grid pattern on the principal surface of the silicon substrate 122, and compose the respective pixels of the wavefront modulator 12. The transparent electrode 125 is arranged on a surface of the transparent substrate 121 that is opposed to the plurality of pixel electrodes 123. The liquid crystal portion 124 is arranged between the plurality of pixel electrodes 123 and the transparent electrode 125. The orientation film 126a is arranged between the liquid crystal portion 124 and the transparent electrode 125, and the orientation film 126b is arranged between the liquid crystal portion 124 and the plurality of pixel electrodes 123. The dielectric mirror 127 is arranged between the orientation film 126b and the plurality of pixel electrodes 123. The dielectric mirror 127 reflects the optical image L1 having entered from the transparent substrate 121 and transmitted through the liquid crystal portion 124 so as to exit again from the transparent substrate 121.

Also, the wavefront modulator 12 further includes a pixel electrode circuit (active matrix driving circuit) 129 that controls a voltage to be applied between the plurality of pixel electrodes 123 and the transparent electrode 125. When voltage is applied to any pixel electrode 123 from the pixel electrode circuit 129, the refractive index of the liquid crystal portion 124 on the pixel electrode 123 changes according to the level of an electric field generated between the pixel electrode 123 and the transparent electrode 125. Thus, the optical path length of the optical image L1 that is transmitted through that part of the liquid crystal portion 124 changes, and accordingly, the phase of the optical image L1 changes. Moreover, by applying various levels of voltages to the plurality of pixel electrodes 123, a spatial distribution of the phase modulation amount can be electrically written, and various wavefront shapes can be realized as appropriate.

FIG. 1 is referred to again. In this adaptive optics system 10A, first, an optical image L1 from a light source or an observation object, which is not shown, enters the wavefront modulator 12 as substantially parallel light. Then, the optical image L1 modulated by the wavefront modulator 12 enters the beam splitter 14 through the relay lenses 15 and 16, and is split into two optical images. One of the split optical images L1 enters the wavefront sensor 11. Then, data including a wavefront shape (e.g., a phase distribution) of the optical image L1 is obtained in the wavefront sensor 11, and a measurement signal S1 indicating the result is provided for the control section 13A. The control section 13A calculates a wavefront shape (phase distribution) of the optical image L1 as necessary based on the measurement signal S1 from the wavefront sensor 11, and outputs a control signal S2 including a pattern for appropriately compensating for a wavefront distortion of the optical image L1 to the wavefront modulator 12. Thereafter, the optical image L1 free from distortion having been compensated for by the wavefront modulator 12 is split by the beam splitter 14, and enters the photodetector through an optical system, which is not shown, to be imaged.

Here, coordinate systems on a modulation plane of the wavefront modulator 12 and a detection plane of the wavefront sensor 11 are set as follows. That is, two directions parallel to the modulation plane of the wavefront modulator 12 and orthogonal to each other are defined as the x-axis direction and y-axis direction in the modulation plane, and two directions parallel to the detection plane of the wavefront sensor 11 and orthogonal to each other are defined as the x-axis direction and y-axis direction in the detection plane. In addition, the x-axis in the modulation plane of the wavefront modulator 12 and the x-axis in the detection plane of the wavefront sensor 11 are in opposite directions to each other, and the y-axis in the modulation plane of the wavefront modulator 12 and the y-axis in the detection plane of the wavefront sensor 11 are in opposite directions to each other. Further, the coordinates having an origin at the center of the modulation plane of the wavefront modulator 12 are provided as (Xs, Ys), and the coordinates having an origin at the center of the detection plane of the wavefront sensor 11 are provided as (Xc, Yc).

At this time, the phase of the wavefront at the position (Xs, Ys) on the modulation plane of the wavefront modulator 12 is mapped one-to-one to the phase of the wavefront at the position (Xc, Yc) on the detection plane of the wavefront sensor 11, and if the modulation plane and detection plane have no rotational displacement, the relationship of these is expressed by the following formula (1).

[Formula 1]

$$Xs = \frac{Xc}{M} + Xs_0 \qquad (1)$$
$$Ys = \frac{Yc}{M} + Ys_0$$

Here, M denotes the magnification of the relay lenses 15, 16. Further, ($Xs_0$, $Ys_0$) are coordinates on the modulation plane of the wavefront modulator 12 projected onto the coordinate origin on the detection plane of the wavefront sensor 11, and represent a positional deviation amount between the modulation plane and detection plane. Because the magnification M is known in most cases, if the modulation plane and detection plane have no rotational displacement, adjustment (calibration) of the adaptive optics system 10A corresponds to checking the value of the above ($Xs_0$, $Ys_0$), and making this value approximate zero (or taking the value of the above ($Xs_0$, $Ys_0$) into consideration when coordinating a pattern that is provided to the wavefront modulator 12 and a wavefront shape that is obtained from the wavefront sensor 11).

In the method for adjusting an adaptive optics system according to the present embodiment, by causing the wavefront modulator 12 to display a special pattern for adjustment and detecting features caused by the pattern in the wavefront sensor 11, a positional deviation amount of a wavefront shape that is measured in the wavefront sensor 11 and a pattern that is displayed on the wavefront modulator 12 is obtained, and adjustment (calibration) is performed based on the positional deviation amount.

Specifically, the control section 13A generates a pattern including a singularity at a predetermined position (hereinafter, referred to as a singularity generation pattern), and sends a control signal indicating the singularity generation pattern to the wavefront modulator 12. As an example of the singularity generation pattern, for example, a hologram to generate a mode of a Laguerre-Gaussian beam having a spiral wavefront shape can be mentioned. The wavefront modulator 12 displays the singularity generation pattern. Then, the wavefront sensor 11 measures a wavefront shape of the optical image L1 under the influence of the singularity generation pattern (hereinafter, referred to as an adjustment wavefront shape) output from the wavefront modulator 12, and provides a measurement signal S1 indicating the measurement result to the control section 13A. The control section 13A detects a singularity based on the measurement signal S1 obtained from the wavefront sensor 11. Then, the control section 13A performs calibration by making a center position of the singularity and a center position of a singularity of the singularity generation pattern that is displayed on the wavefront modulator 12 correspond to each other.

Here, the detection of a singularity in the control section 13A is preferably performed by, for example, calculating a closed-path integration for each of the unit regions composing the wavefront sensor 11 in an adjustment phase distribution from phase gradients measured by the wavefront sensor 11, and determining a distribution of the closed-path integration values. In addition, the unit region mentioned here corresponds to a region that one lens 114 occupies in the lens array 110 composing the wavefront sensor 11. That is, a position of a singularity can be detected assuming that the singularity is included within the unit region of a peak position, which is determined to be the position of a unit region where the closed-path integration value peaks (hereinafter, referred to as a peak position). Further, a more detailed position of the singularity within the unit region of the peak position can be calculated based on closed-path integration values of unit regions located around the peak position.

The method for detecting a singularity by such closed-path integration will be described in greater detail. In general, an integration value of the phase gradient of a phase function along a closed path is determined by the following formulas (2) and (3).

[Formula 2]

$$\oint_C \nabla \phi \cdot d\vec{l} = 2\pi m \quad (2)$$

[Formula 3]

$$\nabla \phi = \frac{\partial \phi}{\partial x}\vec{x} + \frac{\partial \phi}{\partial y}\vec{y} \quad (3)$$

Here, "$\nabla \phi$" denotes a phase gradient (first-order differential) of a phase distribution $\phi$. Further, C denotes a certain closed path in a plane formed by the x-axis and y-axis orthogonal to each other, dl denotes a minute integration line element along the closed path C, and m is an integer.

The above formulas (2) and (3) mean that the closed-path integration value of the phase gradient is m times $2\pi$. Here, the integer m denotes a total topological charge of a singularity(s) in a region surrounded by the closed path C. If there is no singularity in the region surrounded by the closed path C, the closed-path integration value of the above formula (2) becomes zero. On the other hand, if a singularity exists in the region surrounded by the closed path C, the closed-path integration value of the above formula (2) does not become zero. Thus, calculating a closed-path integration value of the phase gradient reveals whether a singularity exists in the region surrounded by the closed path C.

However, with the method described above, a detailed position of the singularity in the region surrounded by the closed path C is unknown.

In general, three or more sampling points are required for identifying one closed path, but the positional accuracy of a singularity to be obtained by the method described above is merely the degree of sampling intervals. That is, the positional accuracy of a singularity is merely an accuracy equivalent to the spatial resolution of the wavefront sensor 11, and for example, when a Shack-Hartmann type wavefront sensor is used as the wavefront sensor 11, this positional accuracy is equal to the pitch of the lens array 110 contained in the wavefront sensor 11. Thus, for improving the positional accuracy of a singularity, it is desirable that, for example, the pitch of the lens array 110 in the wavefront sensor 11 is as small as possible. However, the specifications of the lens array 110 including the pitch are determined mainly by the magnitude of a distortion of the wavefront to be measured, and accordingly, it is not easy to change the pitch of the lens array 110.

Further, a continuous integration formula as the above formula (2) is effective in a theoretical analysis, but practically, a discrete integration formula like the following formula (4) is often used in place of the continuous integration formula. D (i, j) to be determined by the formula (4) is an approximation of the formula (2) to be exact, but practically, it may be just as well to call this a closed-path integration value. Hereinafter, a closed-path integration value that is calculated using such a discrete formula as the formula (4) will be called a circulation value.

[Formula 4]

$$D(i, j) = \frac{w}{2}(G_x(i, j) + G_x(i+1, j) + G_y(i+1, j) + G_y(i+1, j+1) - G_x(i+1, j+1) - G_x(i, j+1) - G_y(i, j+1) - G_y(i, j)) \quad (4)$$

Figure 5:
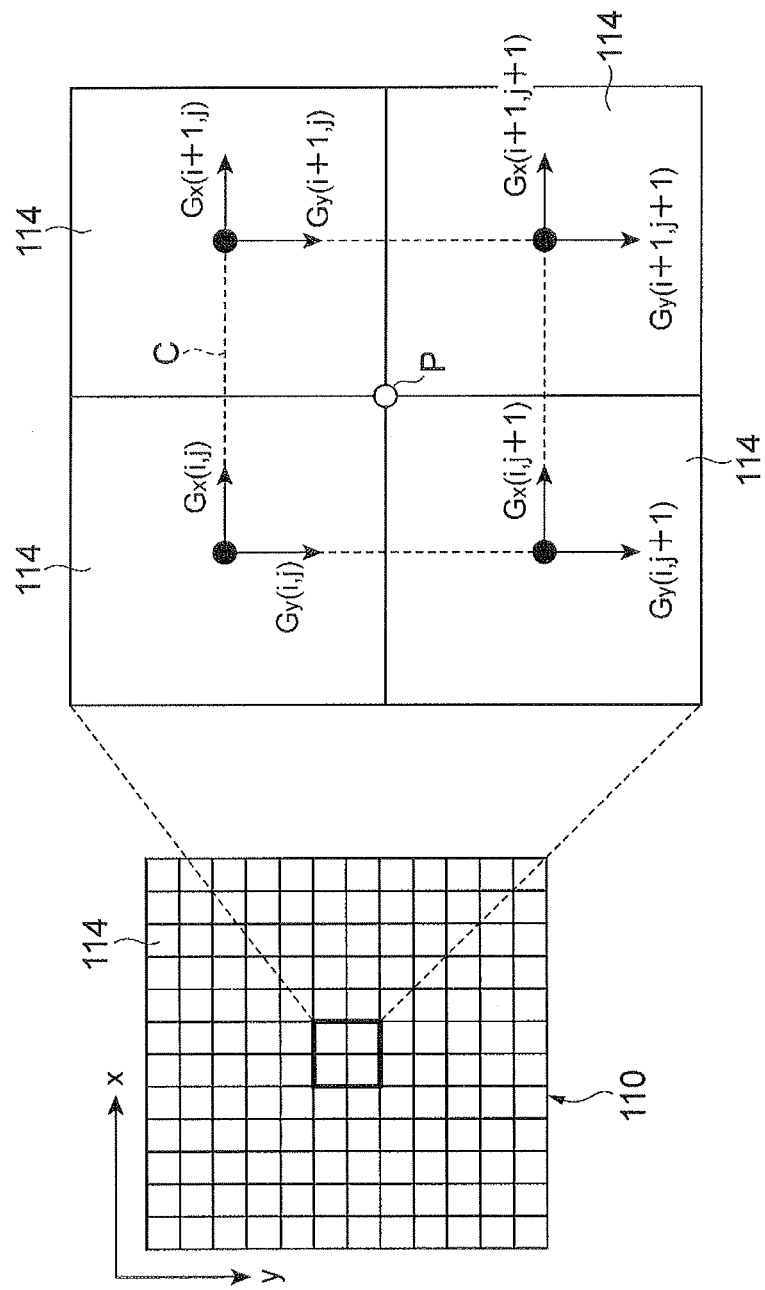
FIG. 5 is a view showing a path of a circulation value determined by the formula (4).

In addition, in the above formula (4), w denotes the pitch of the lenses 114 of the wavefront sensor 11, (i, j) denotes the position of each lens 114 of the wavefront sensor 11, and Gx (i, j) and Gy (i, j) respectively denote an x-component and y-component of a phase gradient measured at each lens position (i, j). The components Gx (i, j) and Gy (i, j) of a phase gradient measured at each lens position (i, j) are average values of first-order differentials of a phase distribution in a unit wavefront divided by each lens (refer to the following formula (5)). Further, the circulation value D (i, j) to be determined by the formula (4) is, as shown in FIG. 5, a value along the path C of a quadrangle (that is, a unit region described above) connecting the centers of 2×2 lenses 114 adjacent to each other.

[Formula 5]

$$\vec{G}^{m,n} = \frac{\int_\Omega \nabla \phi(\vec{x}) d^2 x}{\int_\Omega d^2 x} \approx \frac{k}{f}\left(\frac{\int_H I(\vec{u})\vec{u} d^2 u}{\int_H I(\vec{u}) d^2 u} - \vec{u}_0^{m,n}\right) \quad (5)$$

Figure 6:
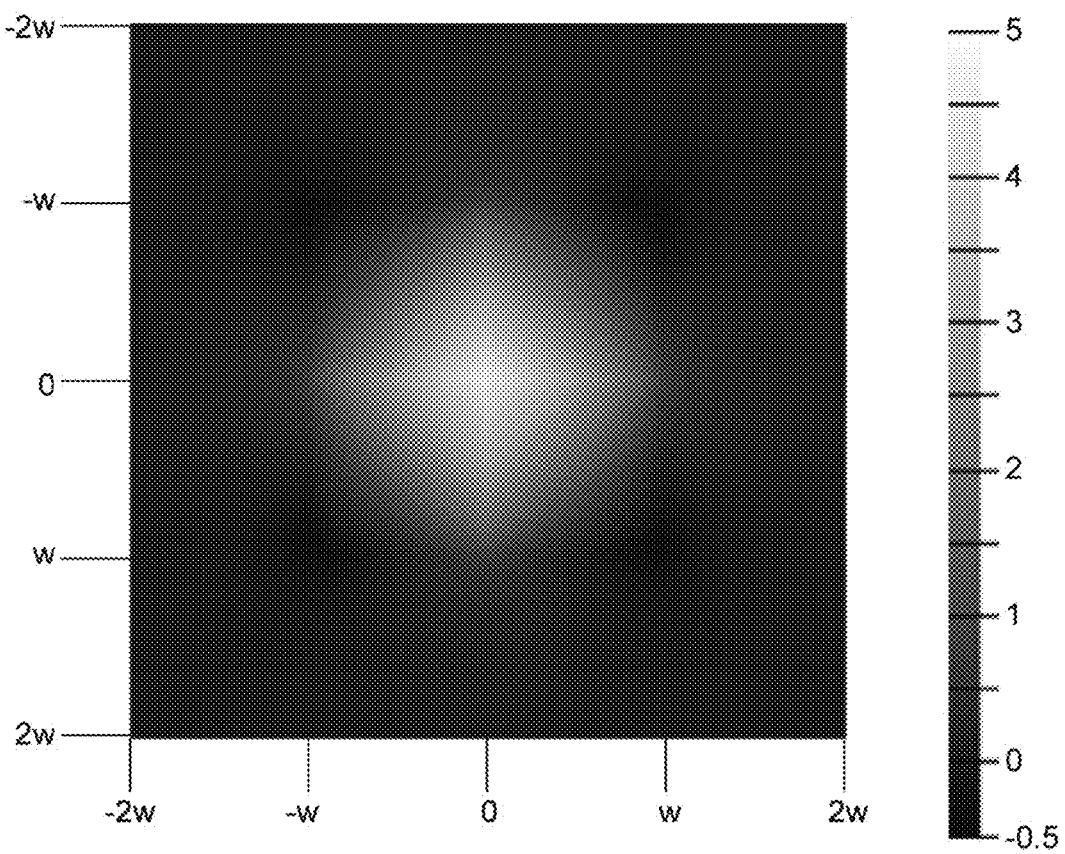
FIG. 6 is a view showing a distribution of circulation values obtained as a result of numerical calculation performed with a singularity position changed variously.

Further, FIG. 6 is a view showing a distribution of circulation values obtained as a result of numerical calculation performed with a singularity position changed variously. In addition, in FIG. 6, the vertical axis and horizontal axis are the same as the x-axis and y-axis in FIG. 5. Further, in FIG. 6, the level of the circulation value is shown by color tones, and the brighter the region, the greater the circulation value. As is apparent from FIG. 6, the circulation value greatly differs depending on the position of the singularity. The circulation value is maximized when the singularity exists at the center of the closed path (that is, when being coincident with a lens intersection), and the circulation value becomes smaller with distance from that position.

In the present embodiment, the circulation value D (i, j) is calculated for each of such unit regions composing the wavefront sensor 11 in an adjustment phase distribution, and a distribution of the circulation values D (i, j) is determined. Then, a peak position of the circulation value D (i, j) is determined, and the position of the singularity is identified within the unit region of the peak position. Further, a more detailed position of the singularity within the unit region of the peak position can be calculated based on circulation values of unit regions located around the peak position. In addition, a detailed method therefor will be described in detail in the following respective examples and modified examples.

First Example

Figure 7:
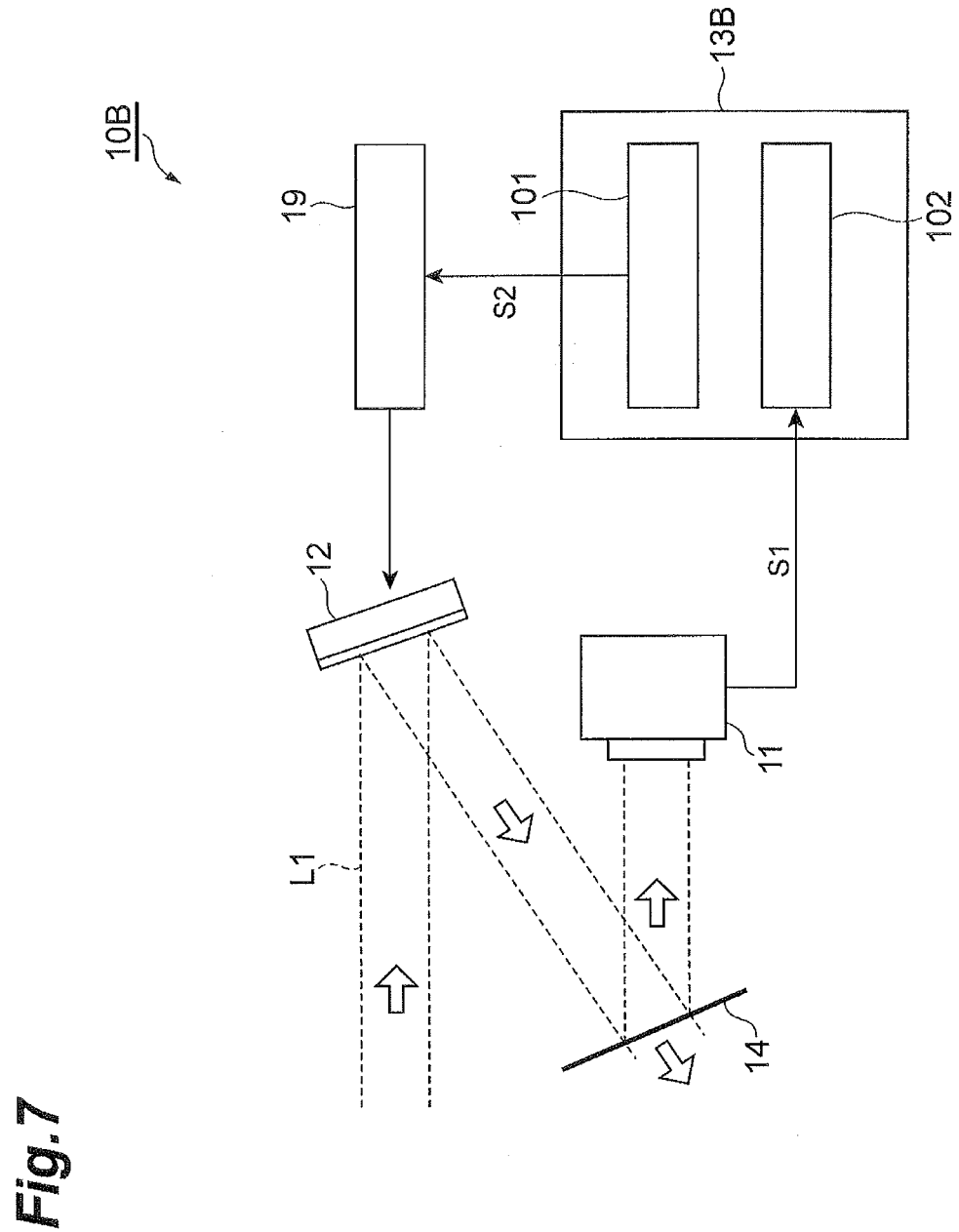
FIG. 7 is a view showing a configuration of an adaptive optics system in a first example.

Now, a first example of a method for adjusting an adaptive optics system according to the present invention will be described. FIG. 7 is a view showing a configuration of an adaptive optics system 10B in the present example. As shown in FIG. 7, the adaptive optics system 10B includes a wavefront sensor 11, a wavefront modulator 12, a control section 13B, a beam splitter 14, and a control circuit section 19. Here, the detailed configuration of the wavefront sensor 11 and the wavefront modulator 12 is the same as that of the above-described embodiment. In addition, the control circuit section 19 is an electronic circuit that receives a control signal S2 from the control section 13B, and provides voltages based on the control signal S2 to the plurality of electrodes of the wavefront modulator 12.

Figure 8:
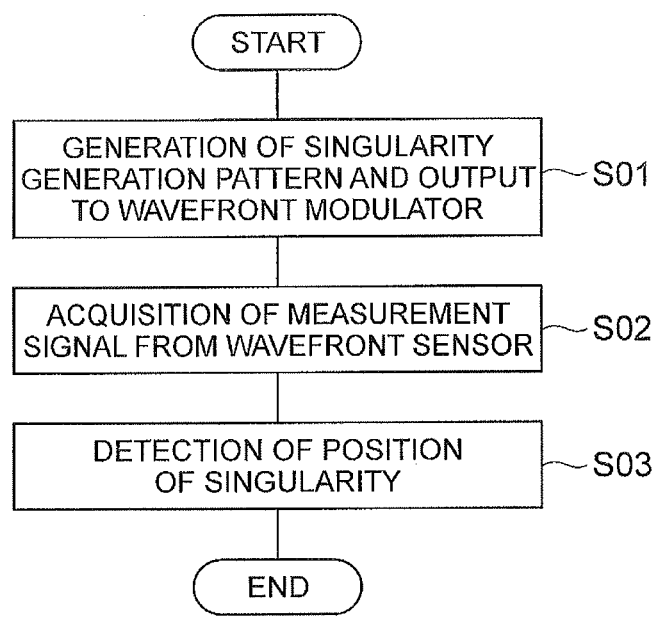
FIG. 8 is a flowchart showing an adjustment method (calibration method) in the adaptive optics system according to the first example.

The control section 13B of the present example includes a singularity generation pattern preparing section 101 and a singularity detecting section 102. In the following, details of the configuration and operation of these will be described. In addition, FIG. 8 is a flowchart showing an adjustment method (calibration method) in the adaptive optics system 10B.

The singularity generation pattern preparing section 101 is a section that prepares a singularity generation pattern in the control section 13B. The singularity generation pattern that the singularity generation pattern preparing section 101 prepares is, for example, a hologram having a spiral phase distribution as shown in the following formula (6). An optical image to be generated by the singularity generation pattern shown by the formula (6) is a Laguerre-Gaussian (LG) mode beam (also called an optical vortex beam) having a radial index p=0 and an azimuthal index q=m.

[Formula 6]

$$\phi(r, \theta) = M(\theta + \theta_0) = m\left(\arctan\frac{y - y_0}{x - x_0} + \theta_0\right) \quad (6)$$

Here, in the formula (6), it is provided that

[Formula 7]

$$\tan(\theta) = \frac{y - y_0}{x - x_0} \quad (7)$$

$$r = \sqrt{(x - x_0)^2 + (y - y_0)^2}$$

In addition, the range of arctan( ) is 0 to $2\pi$. $\theta_0$ denotes a certain constant.

In the above formulas (6) and (7), (x, y) denotes variables of pixel coordinates in the wavefront modulator 12, $(x_0, y_0)$ are coordinates of a center point of a spiral phase distribution, and (r, $\theta$) denotes variables of polar coordinates having an origin at the center point $(x_0, y_0)$. Further, m denotes a topological charge representing the order of a singularity to be generated, and is an integer other than zero. If m is positive, the phase distribution to be expressed by the above formula (6) is a clockwise spiral phase distribution, and it is a counterclockwise spiral phase distribution if m is negative.

In the present example, the singularity generation pattern preparing section 101 generates a control signal S2 to produce a phase distribution as in the formula (6), for example. The control signal S2 is output to the control circuit section 19, and the control circuit section 19 applies voltages based on the control signal S2 to the respective pixel electrodes of the wavefront modulator 12 (step S01 in FIG. 8, the first step). Further, in parallel therewith, light for calibration is made incident onto the wavefront modulator 12. The light for calibration is phase-modulated by the spiral phase distribution presented in the wavefront modulator 12, and then exits from the wavefront modulator 12. At this time, an optical image to exit from the wavefront modulator 12 is an optical vortex beam having a singularity. This optical image enters the wavefront sensor 11. The wavefront sensor 11 measures the optical image to output a measurement signal S1 (step S02 in FIG. 8, the second step).

In the case of absence of a medium to cause discontinuity of the phase distribution of light between the wavefront modulator 12 and the wavefront sensor 11, light to enter the wavefront sensor 11 has a spiral phase distribution, which is substantially the same as that of light immediately after exiting from the wavefront modulator 12. This optical image is detected by the wavefront sensor 11.

In addition, the absence of a medium to cause discontinuity of the phase distribution of light means that a scattering medium that greatly disturbs the amplitude distribution and phase distribution of light is absent. Because optical elements such as, for example, lenses and mirrors do not greatly disturb the phase of light, these optical elements may be arranged between the wavefront modulator 12 and the wavefront sensor 11.

The singularity detecting section 102 detects the position of the singularity by, for example, the closed-path integration method of a phase gradient as in the foregoing (step S03 in FIG. 8, the third step). In the following, details of the method for detecting the position of the singularity in the singularity detecting section 102 will be described.

Now, it is assumed in the lens array 110 of the wavefront sensor 11 that the plurality of lenses 114 are arrayed in a two-dimensional grid pattern (M rows and N columns) with equal intervals. At this time, as shown in FIG. 5, a circulation value of a phase gradient along the closed path (unit region) C surrounding an intersection (hereinafter, referred to as a lens intersection) P of the four lenses 114 adjacent to each other is determined by the foregoing formula (4).

In addition, the circulation value of a phase gradient to be calculated by the formula (4) is not an integral multiple of $2\pi$, but changes depending on the position of a singularity. Specifically, when the singularity is present at the center of the closed path C, that is, when the singularity is coincident with the lens intersection P, the circulation value of the phase gradient is maximized. Moreover, the circulation value of the phase gradient becomes smaller as the singularity separates from the lens intersection P. Such characteristics of the circulation value are effects that are obtained by averaging and discretization of the wavefront sensor 11.

Figure 9:
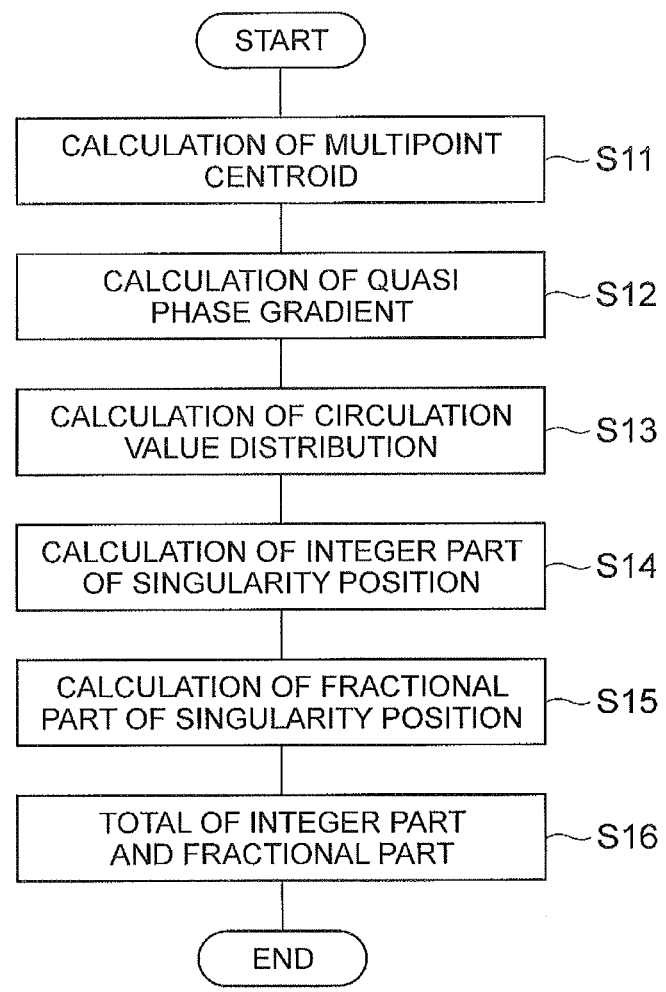
FIG. 9 is a flowchart showing a singularity detection method according to the first example.

In the present example, a singularity is detected using a method to be described in the following. FIG. 9 is a flowchart showing a singularity detection method according to the present example.

<Calculation of Multipoint Centroid>

First, a multipoint centroid is calculated (step S11 in FIG. 9). Now, a multipoint image indicated by a measurement signal S1 obtained from the wavefront sensor 11 is provided as I (u, v). Centroid coordinates ($u_c$ (i, j), $v_c$ (i, j)) of a point image formed by a certain lens (i, j) are calculated by the following formulas (8) and (9). Here, $A_{ij}$ denotes a region of the lens (i, j) projected on the light receiving surface 112a of the image sensor 112. Further, (u, v) are pixel coordinates of the image sensor 112. Hereinafter, the pixel (u, v) will be called a measurement point.

[Formula 8]

$$u_c(i, j) = \frac{\sum_{A_{ij}} uI(u, v)}{\sum_{A_{ij}} I(u, v)} \quad (8)$$

[Formula 9]

$$v_c(i, j) = \frac{\sum_{A_{ij}} vI(u, v)}{\sum_{A_{ij}} I(u, v)} \quad (9)$$

In addition, before performing the multipoint centroid calculation described above, preprocessing such as averaging, bias subtraction processing, and noise reduction processing may be performed in the multipoint image I (u, v). Further, the multipoint centroid calculation described above may be performed by a centroid computing circuit incorporated in the image sensor 112.

<Calculation of Quasi Phase Gradient>

Next, calculation of a quasi phase gradient is performed (step S12 in FIG. 9). Now, the reference position of the lens (i, j) is provided as ($u_r$ (i, j), $v_r$ (i, j)). In addition, the reference position ($u_r$ (i, j), $v_r$ (i, j)) is determined based on the structure of the wavefront sensor 11, and is obtained in advance before this calibration work. Typically, the reference position is an intersection of the optical axis of each lens 114 and the light receiving surface 112a of the image sensor 112. Alternatively, substantially parallel light may be made normally incident onto the wavefront sensor 11 in advance, and a centroid position determined by a centroid calculation from a multipoint image recorded at that time may be provided as a reference position. Also, a substantially parallel light beam may be made incident onto the wavefront modulator 12 with a uniform phase pattern being displayed on the wavefront modulator 12, and a centroid position determined by a centroid calculation from a multipoint image output at that time from the wavefront sensor 11 may be provided as a reference position.

The amount of deviation of a point image position from the reference position when light including a singularity entered the lens (i, j) is calculated by the following formula (10).

[Formula 10]

$$S_x(i,j)=u_c(i,j)-u_r(i,j)$$

$$S_y(i,j)=v_c(i,j)-v_r(i,j) \quad (10)$$

In addition, a quasi phase gradient may be calculated using the following formula (11) in place of the above formula (10). In the formula (11), a is an arbitrary constant other than zero. When a=1/f (f denotes a focal length of the lenses 114 of the lens array 110), $S_x$, $S_y$ are actual phase gradients that are measured from a point image deviation.

[Formula 11]

$$S_x(i,j)=a(u_c(i,j)-u_r(i,j))$$

$$S_y(i,j)=a(v_c(i,j)-v_r(i,j)) \quad (11)$$

<Calculation of Circulation Value Distribution>

Subsequently, calculation of a circulation value distribution is performed (step S13 in FIG. 9). That is, a circulation value on a quadrangular closed path C having a center point at the lens intersection P of 2×2 lenses adjacent to each other is calculated (refer to FIG. 5) by using the following formula (12). In addition, in the formula (12), i 0, . . . , N–2, and j=0, . . . , M–2.

[Formula 12]

$$C(i, j) = S_x(i, j) + S_x(i + 1, j) + S_y(i + 1, j) + S_y(i + 1, j + 1) - \\ S_x(i + 1, j + 1) - S_x(i, j + 1) - S_y(i, j + 1) - S_y(i, j) \quad (12)$$

In addition, the center point of the closed path C, that is, the lens intersection P of four lenses can be calculated by the following formula (13).

[Formula 13]

$$u_{cp}=\tfrac{1}{2}(u_r(i,j)+u_r(i+1,j))$$

$$v_{cp}=\tfrac{1}{2}(v_r(i,j)+v_r(i,j+1)) \quad (13)$$

<Calculation of Integer Part of Singularity Position>

Subsequently, calculation of an integer part of the singularity position is performed (step S14 in FIG. 9). A lens position ($i_{max}$, $j_{max}$) where the circulation value peaks (that is, the absolute value is maximized) is determined based on a distribution of circulation values calculated by the formula (12). Then, the position ($u_{c1}$, $v_{c1}$) of a point of intersection of the positions of four lenses ($i_{max}$, $j_{max}$), ($i_{max}+1$, $j_{max}$), ($i_{max}$, $j_{max}+1$), and ($i_{max}+1$, $j_{max}+1$) is calculated by the following formula (14).

[Formula 14]

$$u_{c1}=\tfrac{1}{2}(u_r(i_{max},j_{max})+u_r(i_{max}+1,j_{max}))$$

$$v_{c1}=\tfrac{1}{2}(v_r(i_{max},j_{max})+v_r(i_{max},j_{max}+1)) \quad (14)$$

Here, ($u_r$ ($i_{max}$, $j_{max}$), $v_r$ ($i_{max}$, $j_{max}$)) is a reference position in the case of the lens position ($i_{max}$, $j_{max}$). The position ($u_{c1}$, $v_{c1}$) obtained as a result of the above-described calculation is an integer part of the position coordinates of a singularity.

<Calculation of Fractional Part of Singularity Position>

Subsequently, calculation of a fractional part of the singularity position is performed (step S15 in FIG. 9). That is, a fractional part of the position coordinates of a singularity is calculated based on a distribution of circulation values in the vicinity of the lens position ($i_{max}$, $j_{max}$) where the circulation value peaks calculated in <Calculation of integer part of singularity position>. Specifically, as in the following formula (15), a fractional part ($u_{c2}$, $v_{c2}$) is calculated by performing a centroid calculation in the vicinity of the circulation value C ($i_{max}$, $j_{max}$).

[Formula 15]

$$u_{c2} = \frac{w}{p_{ccd}} \frac{m_x}{m_0}$$
$$v_{c2} = \frac{w}{p_{ccd}} \frac{m_y}{m_0} \quad (15)$$

Here, in the formula (15), w denotes a lens pitch of the lens array 110, and $p_{ccd}$ denotes a pixel pitch of the image sensor 112. Further, $m_0$ is a 0th-order moment that is calculated in the vicinity of the circulation value C ($i_{max}$, $j_{max}$), and $m_x$ and $m_y$ are first-order moments in the x-direction and y-direction, respectively. For example, in the case of a centroid calculation in a 3×3 vicinity of the peak position, $m_0$, $m_x$, and $m_y$ are calculated by the following formula (16).

[Formula 16]

$$m_x = \quad (16)$$
$$C(i_{max}+1, j_{max}) + C(i_{max}+1, j_{max}-1) + C(i_{max}+1, j_{max}+1) -$$
$$C(i_{max}-1, j_{max}) - C(i_{max}-1, j_{max}-1) - C(i_{max}-1, j_{max}+1)$$
$$m_y = C(i_{max}+1, j_{max}+1) + C(i_{max}, j_{max}+1) +$$
$$C(i_{max}-1, j_{max}+1) - C(i_{max}+1, j_{max}-1) -$$
$$C(i_{max}, j_{max}-1) - C(i_{max}-1, j_{max}-1)$$
$$m_0 = C(i_{max}+1, j_{max}+1) + C(i_{max}, max+1) +$$
$$C(i_{max}-1, j_{max}+1) + C(i_{max}+1, j_{max}-1) +$$
$$C(i_{max}, j_{max}-1) + C(i_{max}-1, j_{max}-1) +$$
$$C(i_{max}+1, j_{max}) + C(i_{max}, j_{max}) + C(i_{max}-1, j_{max})$$

<Total of Integer Part and Fractional Part>

Lastly, by totaling the integer part and fractional part, the position coordinates of a singularity is determined (step S16 in FIG. 9). That is, as shown in the following formula (17), by determining a sum of the integer part calculated in <Calculation of integer part of singularity position> and the fractional part calculated in <Calculation of fractional part of singularity position>, an accurate position of the singularity is calculated.

[Formula 17]

$$u_c = u_{c1} + u_{c2}$$
$$v_c = v_{c1} + v_{c2} \quad (17)$$

That is, the position of the singularity calculated by the present example is ($u_c$, $v_c$) of the formula (17). This singularity is generated by a spiral phase pattern centered at the position ($x_0$, $y_0$) on the wavefront modulator 12. Thus, the coordinates ($u_c$, $v_c$) on the detection plane of the wavefront sensor 11 correspond to the coordinates ($x_0$, $y_0$) on the modulation plane of the wavefront modulator 12.

In addition, if the corresponding relationship of position coordinates ($u_{cP}$, $v_{cP}$) on the detection plane of the wavefront sensor 11 and position coordinates ($x_{0P}$, $y_{0P}$) on the modulation plane of the wavefront modulator 12 is found, the relationship of other arbitrary positions is easily obtained.

Based on the coordinates ($u_c$, $v_c$) on the detection plane of the position of the singularity determined as above and the coordinates ($x_0$, $y_0$) on the modulation plane of the wavefront modulator 12, the control section 13B performs adjustment (calibration) of a positional deviation between the measurement signal S1 that is obtained from the wavefront sensor 11 and the control signal S2 that is sent to the wavefront modulator 12 (the fourth step).

Here, several modified examples regarding a method for detecting a singularity will be described. First, as a first modified example, the following detection method exists.

First Modified Example

In <Calculation of fractional part of singularity position> described above, a circulation value of the position ($i_{max}$, $j_{max}$) where the circulation value peaks and surrounding circulation values adjacent to that position ($i_{max}$, $j_{max}$), that is, 3×3=9 circulation values were used when calculating a 0th-order moment and first-order moments. Without limitation to this method, for example, a part of the nine circulation values (e.g., five or four circulation values) may be used to calculate a 0th-order moment and first-order moments.

For example, when five circulation values out of the nine circulation values are used, a fractional part ($u_{c2}$, $v_{c2}$) is calculated by the following formula (18).

[Formula 18]

$$u_{c2} = \frac{w}{p_{ccd}} \Delta_x$$
$$v_{c2} = \frac{w}{p_{ccd}} \Delta y \quad (18)$$

Here, in the formula (18), w denotes a lens pitch of the lens array 110, and $p_{ccd}$ denotes a pixel pitch of the image sensor 112. Further, $\Delta_x$ and $\Delta_y$ are calculated by, for example, the following formula (19).

[Formula 19]

$$\Delta_x = \frac{C(i_{max}+1, j_{max}) - C(i_{max}-1, j_{max})}{C(i_{max}+1, j_{max}) + C(i_{max}, j_{max}) + C(i_{max}-1, j_{max})} \quad (19)$$
$$\Delta_y = \frac{C(i_{max}, j_{max}+1) - C(i_{max}, j_{max}-1)}{C(i_{max}, j_{max}+1) + C(i_{max}, j_{max}) + C(i_{max}, j_{max}-1)}$$

In addition, when selecting circulation values to be used for the above-described calculation among the nine circulation values, for example, circulation values greater than a preset threshold value may be selected. Alternatively, a predetermined number of circulation values in order from one having the largest value may be selected out of the nine circulation values and used for calculation.

Second Modified Example

Next, as a second modified example, the following detection method is provided. That is, in the above-described example, detection of a singularity is performed by the singularity detecting section 102 of the control section 13B. Without limitation to such a configuration, the adaptive optics system may be arranged so as to perform detection by the singularity detecting section inside the wavefront sensor 11 and so that the wavefront sensor 11 outputs only the result (that is, the position ($u_c$, $v_c$) of a singularity). Alternatively, a part (for example, calculation of a multipoint centroid) of the calculation for detection of a singularity may be performed inside the wavefront sensor 11, and the other processing may be performed in the control section 13B.

Third Modified Example

Next, as a third modified example, the following detection method is provided. That is, in the first example, a fractional part ($u_{c2}$, $v_{c2}$) of the position ($u_c$, $v_c$) of a singularity is determined by a centroid calculation based on a distribution of circulation values in the vicinity of a lens position ($i_{max}$, $j_{max}$) where the circulation value peaks. Besides such a method by a centroid calculation, a fractional part ($u_{c2}$, $v_{c2}$) can be determined by, for example, comparing a theoretical value of a circulation value determined in advance and a circulation value based on a measurement signal S1 from the wavefront sensor 11.

Figure 10:
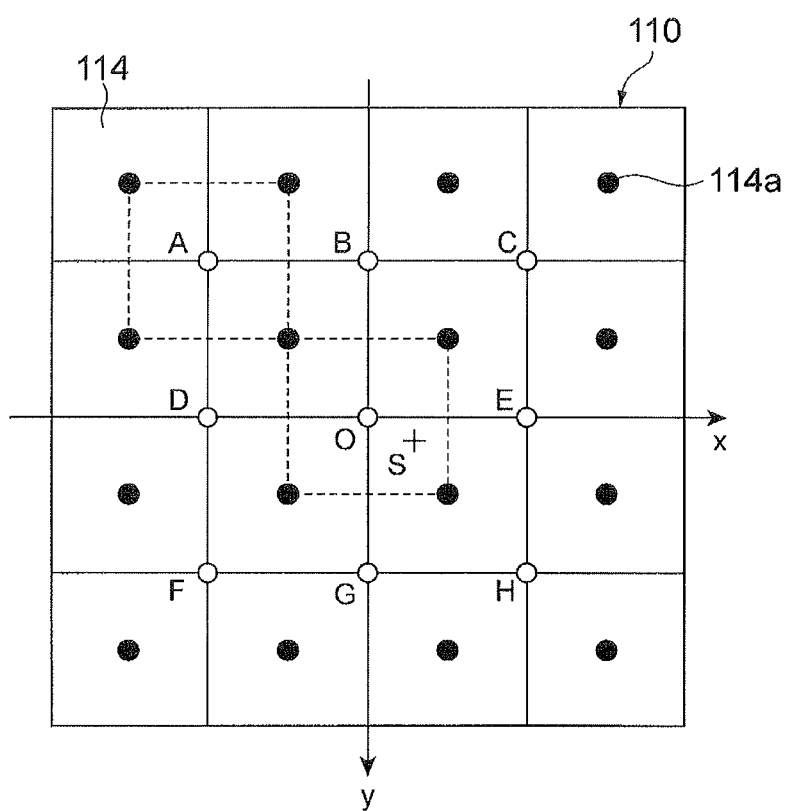
FIG. 10 is a plan view showing 4×4=16 lenses included in the lens array.

First, a method for determining a distribution of theoretical values of circulation values will be described. FIG. 10 is a plan view showing 4×4=16 lenses 114 included in the lens array 110. Now, it is assumed in FIG. 10 that only one singularity S with a topological charge m exists. Then, a lens intersection closest to this singularity S is provided as the coordinate origin O, and an xy orthogonal coordinate system is set as in FIG. 10. In the xy orthogonal coordinate system, the coordinates of the singularity S are denoted by ($x_0$, $y_0$). Further, eight lens intersections that exist around the origin O are respectively provided as A, B, C, D, E, F, G, and H.

At this time, a phase of a point (x, y) is expressed by the following formula (20).

[Formula 20]

$$\phi(x, y; x_0, y_0) = m \cdot \arctan\left(\frac{y - y_0}{x - x_0}\right) \quad (20)$$

Here, the range of arctan( ) is 0 to $2\pi$.

Further, a first-order differential at the point (x, y) is calculated by the following formula (21).

[Formula 21]

$$\frac{\partial \phi}{\partial x} = \frac{-m(y - y_0)}{(x - x_0)^2 + (y - y_0)^2} \quad (21)$$

$$\frac{\partial \phi}{\partial y} = \frac{m(x - x_0)}{(x - x_0)^2 + (y - y_0)^2}$$

Here, each of the phase gradients in the respective lenses 114 to be measured by the wavefront sensor 11 is equal to an average of first-order differentials of a phase distribution inside the lens 114 region. Thus, for example, in the case of a lens array arrangement as in FIG. 10, the phase gradient at a lens (k, l) that is the k-th from the left to right and the l-th from the top to bottom is determined by the following formulas (22) and (23).

[Formula 22]

$$g_x(k, l; x_0, y_0) = \frac{1}{w^2} \int_{y1=(l-1)w}^{y2=lw} \int_{x1=(k-1)w}^{x2=kw} \frac{-m(y-y_0)}{(x-x_0)^2+(y-y_0)^2} dxdy \quad (22)$$

[Formula 23]

$$g_y(k, l; x_0, y_0) = \frac{1}{w^2} \int_{y1=(l-1)w}^{y2=lw} \int_{x1=(k-1)w}^{x2=kw} \frac{m(x-x_0)}{(x-x_0)^2+(y-y_0)^2} dxdy \quad (23)$$

Here, in the formulas (22) and (23), k and l are any of −1, 0, 1, and 2. Further, in FIG. 10, a center point 114a of each lens 114 is shown.

Further, because the origin O is a lens intersection closest to the singularity S, the range of existence of the coordinates ($x_0$, $y_0$) of the singularity is defined by the following formula (24).

[Formula 24]

$$-\frac{w}{2} \leq x_0, y_0 < \frac{w}{2} \quad (24)$$

Thus, a distribution of theoretical values of circulation values is calculated by the following formula (25).

[Formula 25]

$$T(k, l; x_0, y_0) = \quad (25)$$
$$g_x(k, l; x_0, y_0) + g_x(k+1, l; x_0, y_0) + g_y(k+1, l; x_0, y_0) +$$
$$g_y(k+1, l+1; x_0, y_0) - g_x(k+1, l+1; x_0, y_0) -$$
$$g_x(k, l+1; x_0, y_0) - g_y(k, l+1; x_0, y_0) - g_y(k, l; x_0, y_0)$$

Here, in the formula (25), k and l are any of −1, 0, and 1. Further, values to be calculated by the above formula (25) are the following.

T (−1, −1; $x_0$, $y_0$): Circulation value along a quadrangular closed path surrounding the lens intersection A T (0, −1; $x_0$, $y_0$): Circulation value along a quadrangular closed path surrounding the lens intersection B T (1, −1; $x_0$, $y_0$): Circulation value along a quadrangular closed path surrounding the lens intersection C T (−1, 0; $x_0$, $y_0$): Circulation value along a quadrangular closed path surrounding the lens intersection D T (0, 0; $x_0$, $y_0$): Circulation value along a quadrangular closed path surrounding the lens intersection O T (1, 0; $x_0$, $y_0$): Circulation value along a quadrangular closed path surrounding the lens intersection E T (−1, 1; $x_0$, $y_0$): Circulation value along a quadrangular closed path surrounding the lens intersection F T (0, 1; $x_0$, $y_0$): Circulation value along a quadrangular closed path surrounding the lens intersection G T (1, 1; $x_0$, $y_0$): Circulation value along a quadrangular closed path surrounding the lens intersection H The formula (25) provides theoretical values of circulation values at the lens intersection O closest to the singularity S and eight intersections A to H adjacent thereto, a total of nine intersections. Moreover, a distribution of theoretical values of circulation values is dependent on the singularity coordinates ($x_0$, $y_0$). If the singularity coordinates ($x_0$, $y_0$) are determined, a distribution of theoretical values of circulation values is also uniquely determined.

Subsequently, the distribution of theoretical values of circulation values determined by the method described above and a distribution of circulation values that are calculated from the measurement result of the wavefront sensor 11 are compared, and ($x_0$, $y_0$) where a correlation coefficient is maximized is determined. The thus-determined ($x_0$, $y_0$) is a fractional part of the singularity position ($u_c$, $v_c$) of the singularity S.

Specifically, if the position where the circulation value peaks, that is obtained from the measurement result of the wavefront sensor 11, is provided as ($i_{max}$, $j_{max}$), the correlation coefficient R ($x_0$, $y_0$) is determined by the following formula (26).

[Formula 26]

$$R(x_0, y_0) = \frac{\sum_{l=-1}^{1}\sum_{k=-1}^{1}(C(i_{max}+k, j_{max}+l) - \overline{C}) \cdot (T(k, l; x_0, y_0) - \overline{T(x_0, y_0)})}{\sqrt{\sum_{l=-1}^{1}\sum_{k=-1}^{1}(C(i_{max}+k, j_{max}+l) - \overline{C})^2 \times \sum_{l=-1}^{1}\sum_{k=-1}^{1}T(k, l; x_0, y_0) - (\overline{T(x_0, y_0)})^2}} \quad (26)$$

Here, it is provided that

[Formula 27]

$$\overline{C} = \frac{1}{9} \times \sum_{l=-1}^{1}\sum_{k=-1}^{1} C(i_{max}+k, j_{max}+l) \quad (27)$$

[Formula 28]

$$\overline{T(x_0, y_0)} = \frac{1}{9} \times \sum_{l=-1}^{1}\sum_{k=-1}^{1} T(k, l; x_0, y_0) \quad (28)$$

Moreover, the fractional part ($u_{c2}$, $v_{c2}$) of the singularity position ($u_c$, $v_c$) is determined by the following formula (29).

[Formula 29]

$$R(u_{c2}, v_{c2}) = \text{MAX}(R(x_0, y_0)) \quad (29)$$

By summing up the thus-obtained fractional part ($u_{c2}$, $v_{c2}$) and the integer part ($u_{c1}$, $v_{c1}$), the position ($u_c$, $v_c$) of the singularity is obtained.

Although, in the above-described method, a distribution T(k, l; $x_0$, $y_0$) of theoretical values of circulation values is determined by numerical calculation, the distribution T(k, l; $x_0$, $y_0$) of theoretical values of circulation values may be determined from a measurement result that is obtained by making a test pattern where the position ($u_c$, $v_c$) of a singularity is known incident onto the wavefront sensor 11.

Fourth Modified Example

Figure 11:
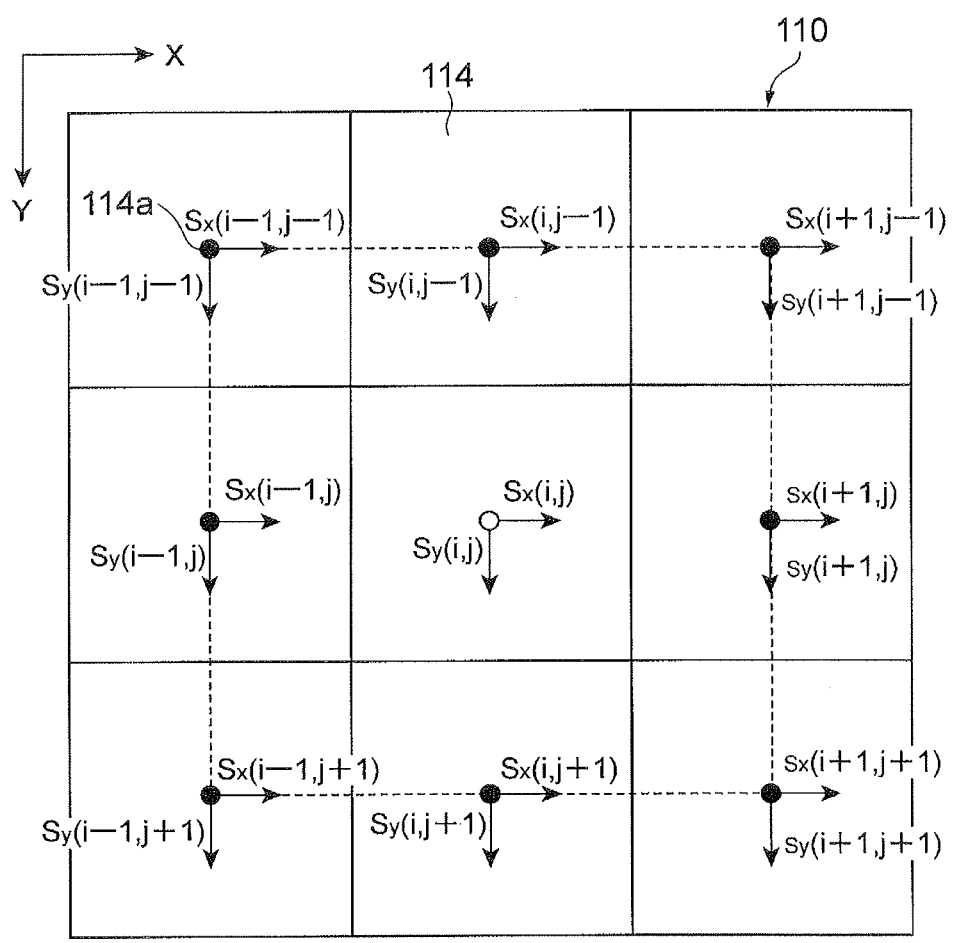
FIG. 11 is a view showing lens regions of 3 rows and 3 columns in the lens array when calculating a circulation value that is a quasi phase gradient integration value.

Next, a fourth modified example will be described. In the present example, as shown in FIG. 11, a circulation value, that is, a quasi phase gradient integration value is calculated using lens regions of 3 rows and 3 columns in the lens array 110. At this time, as a closed path C when calculating the circulation value, a quadrangle centered on a reference position of the central lens 114 is set. The circulation value C (i, j) is determined by the following formula (30).

[Formula 30]

$$\begin{aligned} C(i, j) = \quad & (30) \\ S_x(i-1, j-1) + 2S_x(i, j-1) + S_x(i+1, j-1) + S_y(i+1, j-1) + \\ 2S_y(i+1, j) + S_y(i+1, j+1) - S_x(i-1, j+1) - 2S_x(i, j+1) - \\ S_x(i+1, j+1) - S_y(i-1, j-1) - 2S_y(i-1, j) - S_y(i-1, j+1) \end{aligned}$$

In the first example described above, a circulation value is determined using quasi phase gradients measured in lens regions of 2 rows and 2 columns adjacent to each other. In that case, when a singularity exists in this lens region, the singularity always belongs to the inside of the region of any of the lenses. Thus, at least one of the quasi phase gradients in the respective regions of four lenses is influenced by the singularity. That is, at the center of the singularity, the light intensity becomes zero, and the phase has uncertainty. Due to these characteristics, calculation of the phase gradient may be affected, although slightly.

In contrast thereto, as in the present modified example, as a result of calculating a circulation value using quasi phase gradients of lens regions of 3 rows and 3 columns, a singularity exists only in a central region of the lens regions, and no singularity exists in eight regions therearound. Thus, there is an advantage that it is not influenced by a singularity as described above.

Second Example

Figure 12:
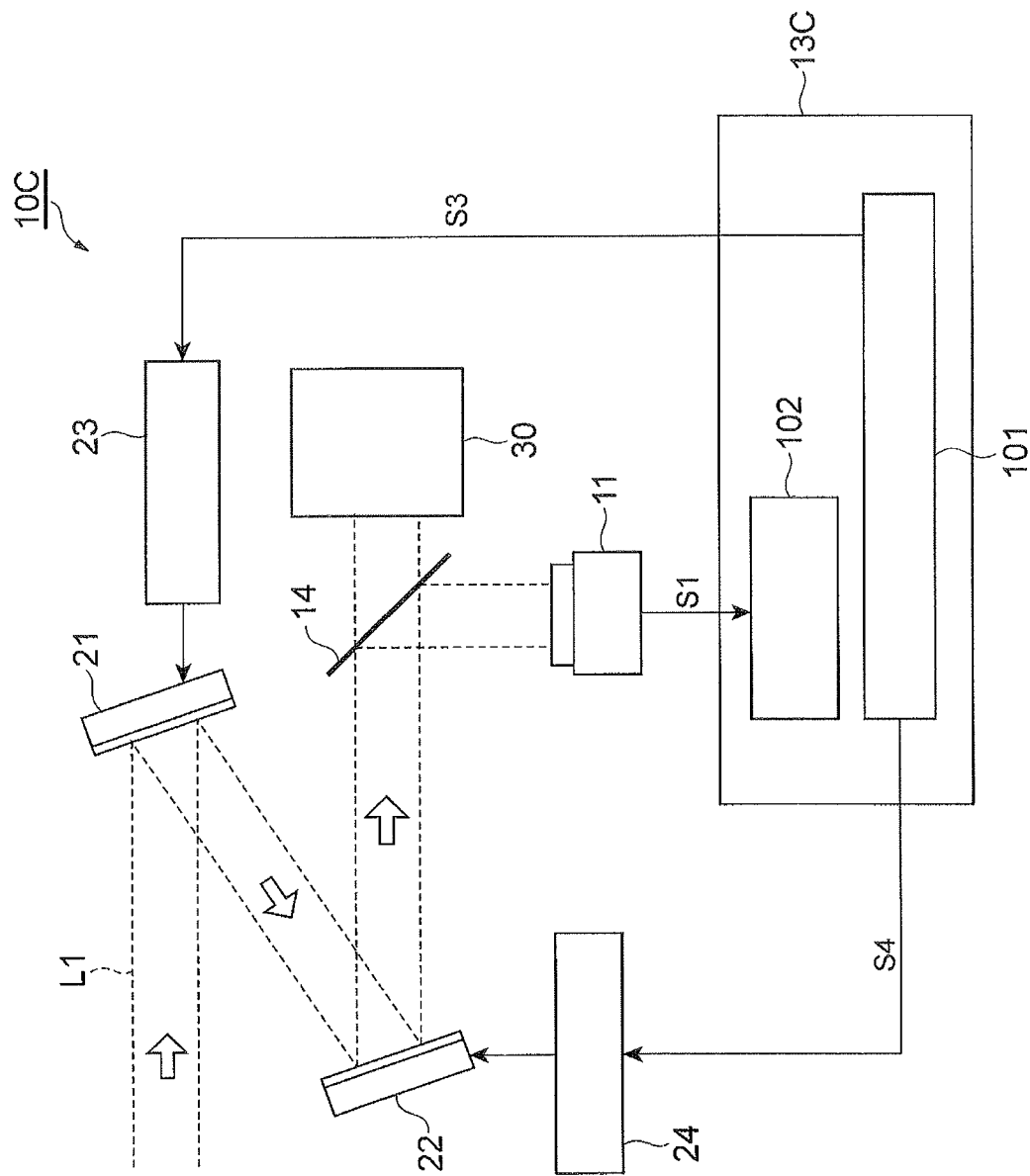
FIG. 12 is a view showing a configuration of an adaptive optics system according to a second example.

FIG. 12 is a view showing a configuration of an adaptive optics system 10C according to a second example of the present invention. The adaptive optics system 10C includes a wavefront sensor 11, a control section 13C, a beam splitter 14, wavefront modulators 21 and 22, and control circuit sections 23 and 24. Here, the detailed configuration of the wavefront sensor 11 is the same as that of the above-described embodiment. Further, the two wavefront modulators 21 and 22 are arranged in the present example, but the detailed configuration of these is the same as that of the wavefront modulator 12 of the above-described embodiment. The control circuit sections 23 and 24 are respectively electronic circuits that receive respective control signals S3 and S4 from the control section 13C, and apply voltages based on the control signals S3 and S4 to the pluralities of electrodes of the respective wavefront modulators 21 and 22.

In this adaptive optics system 10C, first, an optical image L1 from a light source or an observation object, which is not shown, enters the wavefront modulator 21 as substantially parallel light, and receives phase modulation to be reflected. Then, the optical image L1 reflected on the wavefront modulator 21 enters the wavefront modulator 22 through an optical system, which is not shown, and again receives phase modulation to be reflected. The optical image L1 reflected on the wavefront modulator 22 is split into two optical images in the beam splitter 14. One of the split optical images L1 enters a photodetector 30 through an optical system, which is not shown, and is imaged. On the other hand, the other of the split optical images L1 enters the wavefront sensor 11. Then, the shape of a wavefront of the optical image L1 is measured in the wavefront sensor 11, and a measurement signal S1 indicating the measurement result is provided for the control section 13C. The control section 13C calculates the shape of a wavefront of the optical image L1 based on the measurement signal S1 from the wavefront sensor 11, and outputs control signals S3 and S4 for appropriately correcting the wavefront of the optical image L1 to the control circuit sections 23 and 24.

A method for adjusting the adaptive optics system 10C thus including two wavefront modulators 21 and 22 will be described. First, a control signal S3 including a singularity generation pattern prepared in the singularity generation pattern preparing section 101 of the control section 13C is sent to the control circuit section 23. On the wavefront modulator 21, the singularity generation pattern is thereby displayed. Simultaneously, a control signal S4 including a plane wave pattern is sent from the control section 13C to the control circuit section 24. On the wavefront modulator 22, the plane wave pattern is thereby displayed. Then, light is made incident onto the wavefront modulator 21 in this state, and an optical image through the wavefront modulators 21 and 22 is detected in the wavefront sensor 11.

Then, coordinates ($u_{ca}$, $v_{ca}$) of a singularity in the wavefront sensor 11 are detected using a method according to each example or each modified example described above. The coordinates ($u_{ca}$, $v_{ca}$) represent a positional deviation between a control point on the modulation plane of the wavefront modulator 21 and a measurement point on the detection plane of the wavefront sensor 11.

Next, a control signal S3 including a plane wave pattern is sent from the control section 13C to the control circuit section 23. On the wavefront modulator 21, the plane wave pattern is thereby displayed. Simultaneously, a control signal S4 including a singularity generation pattern prepared in the singularity generation pattern preparing section 101 of the control section 13C is sent to the control circuit section 24. On the wavefront modulator 22, the singularity generation pattern is thereby displayed. Then, light is made incident onto the wavefront modulator 21 in this state, and an optical image through the wavefront modulators 21 and 22 is detected in the wavefront sensor 11.

Then, coordinates ($u_{cb}$, $v_{cb}$) of a singularity in the wavefront sensor 11 are detected using a method according to each example or each modified example described above. The coordinates ($u_{cb}$, $v_{cb}$) represent a positional deviation between a control point on the modulation plane of the wavefront modulator 22 and a measurement point on the detection plane of the wavefront sensor 11.

Lastly, by determining a difference between the coordinates ($u_{ca}$, $v_{ca}$) of the singularity on the wavefront sensor 11 regarding the wavefront modulator 21 and the coordinates ($u_{cb}$, $v_{cb}$) of the singularity on the wavefront sensor 11 regarding the wavefront modulator 22, a positional deviation between a control point in the modulation plane of the wavefront modulator 21 and a control point in the modulation plane of the wavefront modulator 22 is determined. In this manner, the corresponding relationship of the two wavefront modulators 21 and 22 can be easily determined.

Based on the corresponding relationship of the two wavefront modulators 21 and 22 determined as above, the control section 13C performs adjustment (calibration) of a positional deviation between the control signal S3 that is sent to the wavefront modulator 21 and the control signal S4 that is sent to the wavefront modulator 22.

Third Example

As a third example, a method for determining the optical imaging magnification M between the wavefront modulator 12 and the wavefront sensor 11 in the first example will be described.

First, in the singularity generation pattern preparing section 101 of the control section 13B, a pattern capable of generating two singularities is prepared. This is, for example, a pattern that can cause a spiral phase pattern LG1 with an azimuthal coefficient m1 to be displayed at a position ($x_1$, $y_1$) of the wavefront modulator 12 and cause a spiral phase pattern LG2 with an azimuthal coefficient m2 to be displayed at a position ($x_2$, $y_2$) different from ($x_1$, $y_1$). Then, by sending a control signal S2 including such a singularity generation pattern to the control circuit section 19, the wavefront modulator 12 is caused to display the spiral phase patterns LG1 and LG2. Then, light is made incident onto the wavefront modulator 12 in this state, and an optical image through the wavefront modulator 12 is detected in the wavefront sensor 11.

At this time, in the detection plane of the wavefront sensor 11, if a center position of an optical vortex generated by the spiral phase pattern LG1 is provided as ($p_1$, $q_1$), and a center position of an optical vortex generated by the spiral phase pattern LG2 is provided as ($p_2$, $q_2$), the optical imaging magnification M is calculated by the following formula (31).

[Formula 31]

$$M = \frac{\sqrt{(p_2 - p_1)^2 + (q_2 - q_1)^2}}{\sqrt{(x_2 - x_1)^2 + (y_2 - y_1)^2}} \tag{31}$$

Further, an optical imaging magnification between the two wavefront modulators 21 and 22 in the second example described above is also easily calculated by the similar method as in the present example.

Fifth Modified Example

Figure 13:
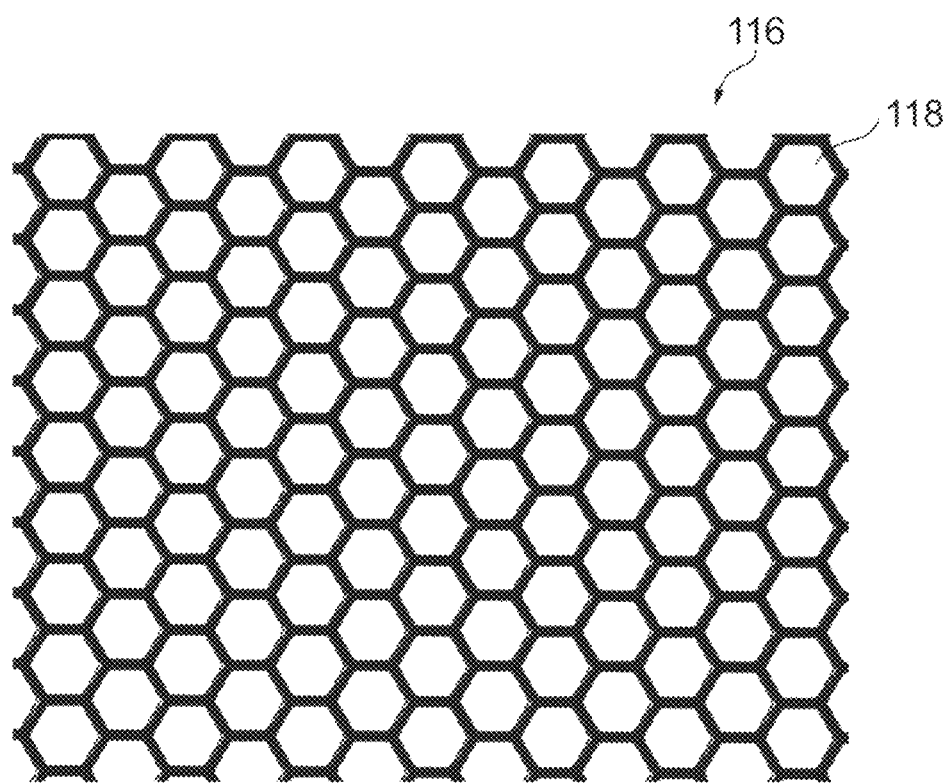
FIG. 13 is a plan view showing a configuration of a lens array of the wavefront sensor, and shows an appearance viewed from the optical axis direction of an optical image that enters the wavefront sensor.

In the foregoing respective examples and modified examples, a configuration of the plurality of lenses 114 arrayed in a two-dimensional grid pattern has been exemplified as the lens array 110 of the wavefront sensor 11, but the lens array of the wavefront sensor 11 is not limited to such a configuration. FIG. 13 is a plan view showing a configuration of a lens array 116 of the wavefront sensor 11 in the present modified example, and shows an appearance viewed from an optical axis direction of an optical image L1 that enters the wavefront sensor 11.

Figure 14:
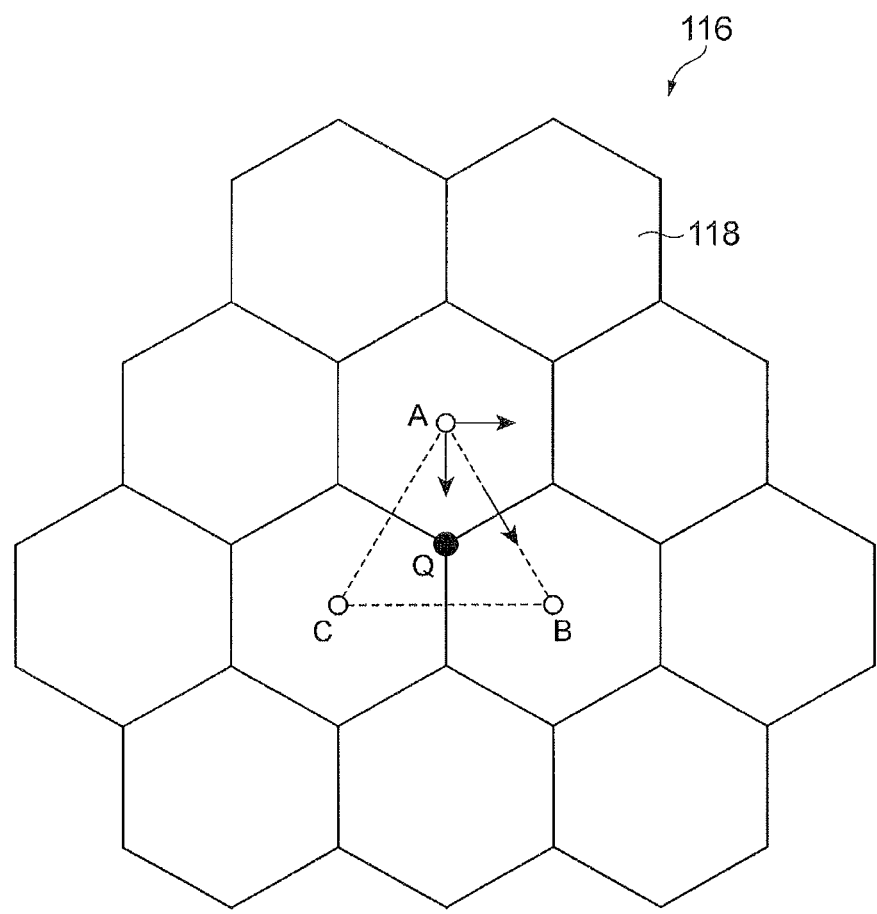
FIG. 14 is a view showing a path connecting the centers of three lenses adjacent to each other.
Figure 15:
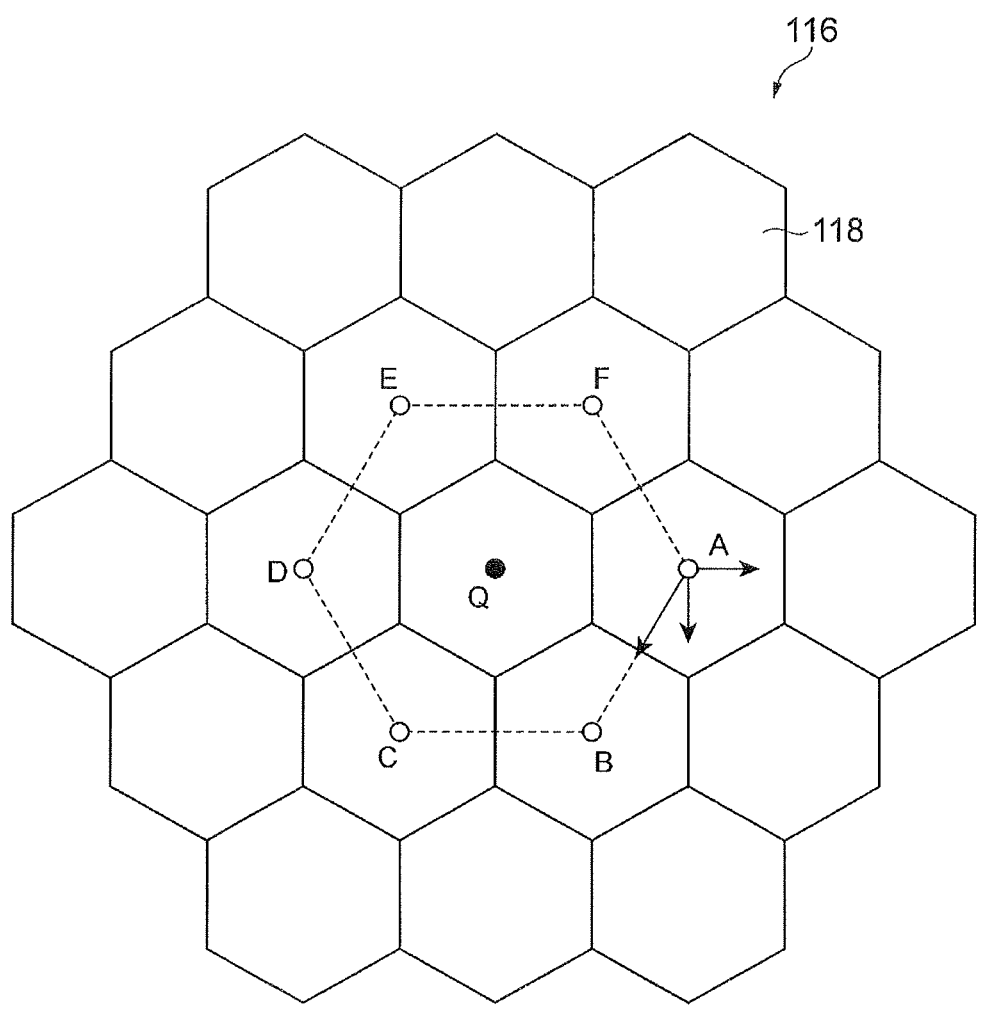
FIG. 15 is a view showing a path connecting the centers of six lenses adjacent around one lens.

As shown in FIG. 13, the lens array 116 of the present modified example has a honeycomb structure in which a plurality of regular hexagonal lenses 118 are arranged without gaps. In this case, as a path of closed-path integration when calculating a singularity position, as shown in FIG. 14, a path connecting the centers of three lenses 118 adjacent to each other (that is, a closed path surrounding a lens intersection Q of three lenses 118) is preferred. Alternatively, as shown in FIG. 15, it may be a path connecting the centers of six lenses 118 adjacent around one lens 118 (that is, a closed path surrounding the center Q of a central lens 118). In the case of a closed path as in FIG. 15, a closed-path integration value can be calculated by the following formula (32).

[Formula 32]

$$\begin{aligned}D(i, j) = b \times \\ (g_x(A)\cos 120° + g_y(A)\cos(30°) + g_x(A)\cos 60° + g_y(A)\cos(230°) + \\ g_x(B)\cos 120° + g_y(B)\cos(30°) + g_x(B)\cos 180° + \\ g_y(B)\cos(90°) + g_x(C)\cos 180° + g_x(C)\cos(90°) + \\ g_x(C)\cos 240° + g_y(C)\cos(150°) + g_x(D)\cos 240° + \\ g_y(D)\cos(150°) + g_x(D)\cos 300° + \\ g_y(D)\cos(210°) + g_x(E)\cos 300° + g_y(E)\cos(210°) + \\ g_x(E)\cos 0° + g_y(E)\cos(270°) + g_x(F)\cos 0° + \\ g_y(F)\cos(270°) + g_x(F)\cos 60° + g_y(F)\cos(230°))\end{aligned} \tag{32}$$

Here, the indexes A to F represent the center points of respective six lenses 118 adjacent around one lens 118.

Sixth Modified Example

In the foregoing respective examples and modified examples, a phase pattern having a spiral phase distribution has been used as a singularity generation pattern, but as the singularity generation pattern, various phase patterns capable of generating singularities can be used, without limitation to such a distribution. For example, a phase pattern in which a phase distribution of a blazed grating or a phase distribution having the Fresnel lens effect is added to a spiral phase distribution is preferred. Further, various other phase patterns that can generate singularities, for example, an ordinary Laguerre-Gaussian (LG) beam forming hologram, may be used.

Seventh Modified Example

In the foregoing respective examples and modified examples, the wavefront modulator 12 and the wavefront sensor 11 are fixed to a non-movable support member, but at least one of the wavefront modulator 12 and the wavefront sensor 11 may be fixed onto a movable support member (e.g., an XY stage). In this case, calibration can be performed by making a position ($u_c$, $v_c$) of a singularity that is calculated by the method of the foregoing respective examples and modified examples and a position of a singularity of the singularity generation pattern that is being displayed on the wavefront modulator 12 correspond to each other, and moving at least one of the wavefront modulator 12 and the wavefront sensor 11 such that these positions approximate each other.

Effects to be obtained by the adaptive optics systems 10A to 10C and methods for adjusting the same according to the above-described embodiment, examples, and modified examples having been described above will be described.

In these adaptive optics systems 10A to 10C and methods for adjusting the same, by causing the wavefront modulator 12 to display a special phase pattern for adjustment (that is, a singularity generation pattern) and then detecting features caused by the phase pattern (that is, a position of a singularity) in the wavefront sensor 11, a positional deviation amount between an adjustment phase distribution that is measured in the wavefront sensor 11 and a singularity generation pattern that is displayed on the wavefront modulator 12 is obtained. Then, a deviation between the measurement signal S1 that is obtained from the wavefront sensor 11 and the control signal S2 that is sent to the wavefront modulator 12 is adjusted based on the positional deviation amount. Alternatively, an adjustment in physical position of the detection plane of the wavefront sensor 11 and the modulation plane of the wavefront modulator 12 is performed.

Thus, according to the adaptive optics systems 10A to 10C and methods for adjusting the same described above, because calculation of a phase distribution from a measurement signal of the wavefront sensor 11 can be omitted, adjustment can be performed at high accuracy without depending on the phase modulation accuracy of the wavefront modulator 12 and the phase measurement accuracy of the wavefront sensor 11. Further, according to the adaptive optics systems 10A to 10C and methods for adjusting the same described above, an adjustment light beam with high accuracy is also unnecessary, and the system configuration can be simplified. Further, calculation of a phase distribution from a measurement signal of the wavefront sensor 11 can be omitted, and it is also unnecessary to repeatedly perform a hologram display and calculation, so that the adjustment time can be shortened.

As above, according to the adaptive optics systems 10A to 10C and methods for adjusting the same described above, a positional deviation between a phase distribution that is measured in the wavefront sensor 11 and a compensation phase pattern that is displayed on the wavefront modulator 12 can be corrected in a short time and with high accuracy.

Here, FIG. 16 includes views explaining advantages of that the accuracy of adjustment (calibration) of the adaptive optics system is high. (a) in FIG. 16 conceptually shows, for comparison, an incoming wavefront 61, a compensating wavefront 62, and a compensated wavefront 63 (the sum of the incoming wavefront 61 and the compensating wavefront 62) when the adjustment accuracy is low. Also, (b) in FIG. 16 conceptually shows an incoming wavefront 71, a compensating wavefront 72, and a compensated wavefront 73 (the sum of the incoming wavefront 71 and the compensating wavefront 72) when the adjustment accuracy is high.

As shown in (a) in FIG. 16, when there is a positional deviation between the incoming wavefront 61 and the compensating wavefront 62 because the adjustment accuracy is low, a distortion of the wavefront is not completely removed in the compensated wavefront 63. Thus, there is a possibility for deterioration in imaging characteristics, and also due to the influence of feedback control, the wavefront distortion may also increase. In contrast, as shown in (b) in FIG. 16, when the adjustment accuracy is high and a positional deviation between the incoming wavefront 71 and the compensating wavefront 72 is small, a wavefront distortion is appropriately corrected, and the compensated wavefront 73 can be substantially a plane wave.

Further, in the adaptive optics systems 10A to 10C and methods for adjusting the same described above, a Shack-Hartmann type wavefront sensor is used as the wavefront sensor 11. Because phase gradients can therefore be directly determined based on deviations from reference positions of a multipoint image formed by the lens array 110, a distribution of phase gradients can be easily obtained.

Further, in the adaptive optics systems 10A to 10C and methods for adjusting the same described above, a singularity position is determined using closed-path integration values (circulation values) of phase gradients. Ordinarily, the wavefront modulator 12 and other optical systems such as lenses, and further, light to enter the wavefront modulator 12 have optical aberration. However, because the ordinary optical aberration has a continuous phase distribution, a closed-path integration value (circulation value) of its phase gradient is always zero, or takes a constant. On the other hand, a non-continuous component (e.g., a singularity component) of the phase distribution is expressed in the closed-path integration value (circulation value) as a significant value. Thus, when the closed-path integration value (circulation value) is zero, it can be judged that a singularity does not exist within a closed path (unit region). Conversely, when the circulation value is not zero, it can be judged that a singularity exists in the closed path, and the position of the singularity can be identified. As above, according to the method for adjusting the adaptive optics system described above, by determining a singularity position using a closed-path integration value (circulation value) of phase gradients, the singularity position can be calculated with accuracy, irrespective of the optical aberration of light for calibration and the wavefront modulator 12 and the like.

Further, in the adaptive optics systems 10A to 10C and methods for adjusting the same described above, a position of a singularity within a closed path of a peak position is calculated based on closed-path integration values (circulation values) of closed paths (unit regions) located around the peak position. A phase gradient to be measured by the wavefront sensor 11 is an average value of first-order differential values in a region defined by each lens 114. Thus, a closed-path integration value (circulation value) of the region is dependent on a relative position of the singularity and the closed path. That is, based on closed-path integration values (circulation values) of closed paths (unit regions) located around a peak position as described above, the position of the singularity can be identified in greater detail.

Here, experimental results to confirm the above-described effects provided by the adaptive optics systems 10A to 10C and methods for adjusting the same described above will be described in the following.

Figure 17:
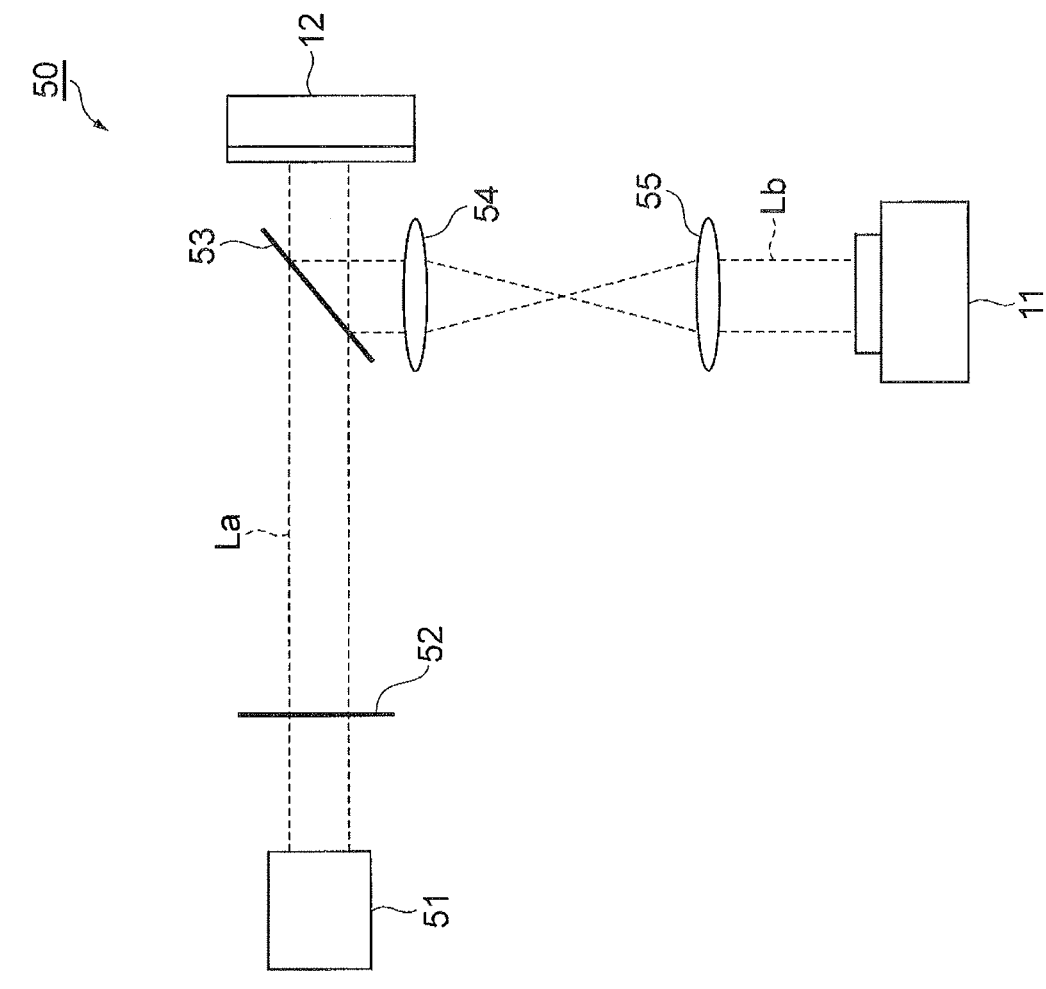
FIG. 17 is a view schematically showing a configuration of an optics system used for experiment.

FIG. 17 is a view schematically showing a configuration of an optics system 50 used for the present experiment. The optics system 50 includes a wavefront sensor 11, a wavefront modulator 12, a light source 51, an aperture 52, a beam splitter 53, and a relay optical system consisting of two lenses 54 and 55. Here, the detailed configuration of the wavefront sensor 11 and the wavefront modulator 12 is the same as that of the embodiment described above.

The light source 51 emits laser light La having a wavelength of 633 nm. The laser light La is substantially parallel light. The laser light La passes through the aperture 52, and is transmitted through the beam splitter 53 to enter the wavefront modulator 12. Then, the laser light La is reflected and modulated by the wavefront modulator 12, and output from the wavefront modulator 12 as an optical image Lb. The optical image Lb is reflected on the beam splitter 53, and passes through the lenses 54 and 55 to enter the wavefront sensor 11. The wavefront sensor 11 outputs data representing a distribution of phase gradients of the optical image Lb. Here, the wavefront sensor 11 is arranged at an optically conjugate plane of the wavefront modulator 12.

Figure 18:
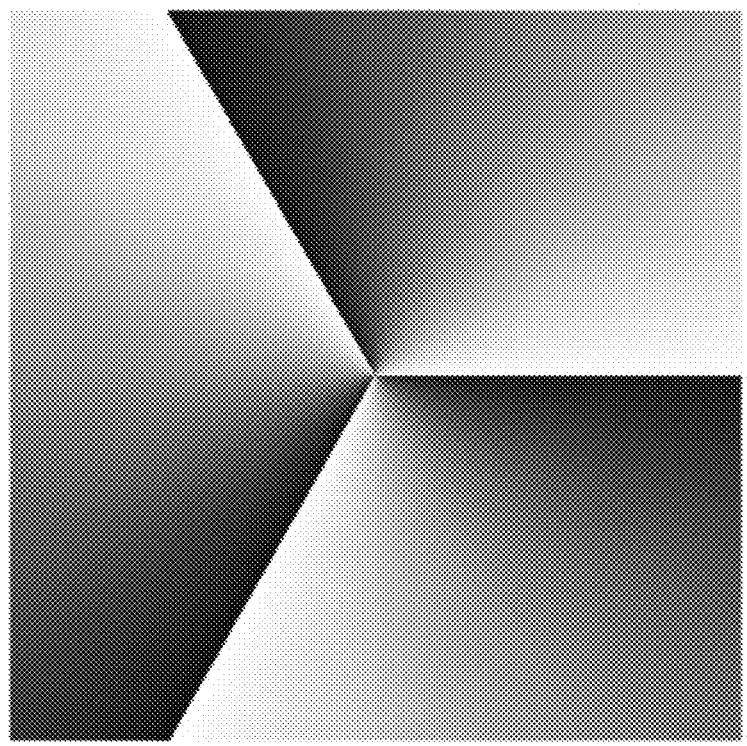
FIG. 18 is a view showing an example of a singularity generation pattern that the wavefront modulator is caused to display in the experiment.

FIG. 18 is a view showing an example of a singularity generation pattern that the wavefront modulator 12 is caused to display in the present experiment. Here, in FIG. 18, the level of the phase of a singularity generation pattern is shown by tones, and the phase of the darkest part is 0 (rad), and the phase of the brightest part is $2\pi$ (rad). Also, the boundary of the dark color and bright color is a part where the phase changes from $2\pi$ (rad) to 0 (rad), and the phase in that part is continuous in actuality. That is, the singularity generation pattern shown in FIG. 18 has a clockwise spiral phase distribution, and has three boundaries in one round, so that the topological charge of this singularity generation pattern is 3. Moreover, a center part of the spiral corresponds to a singularity.

Figure 19:
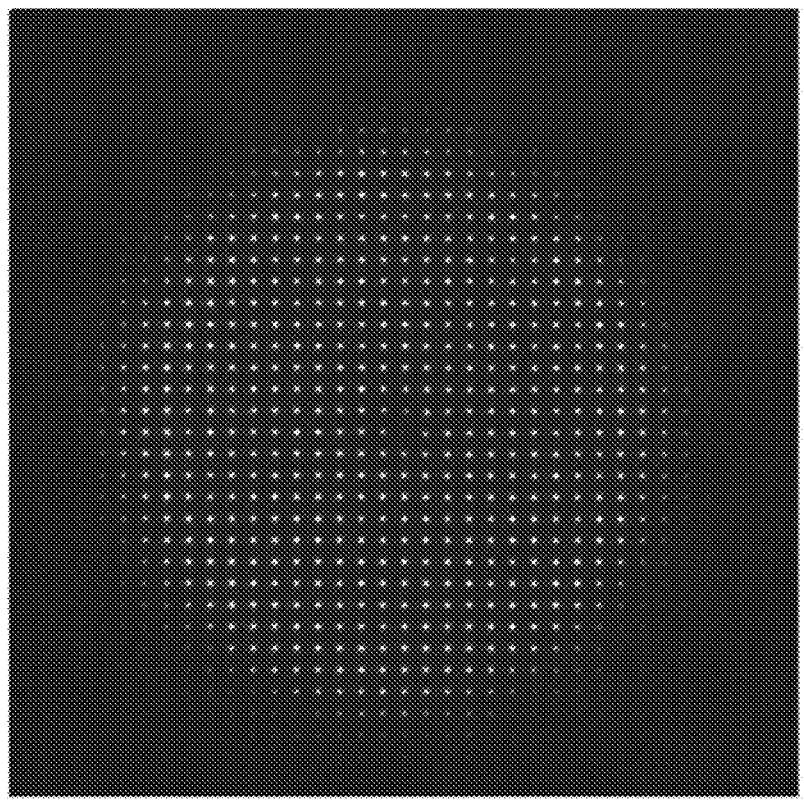
FIG. 19 is a view showing an example of a multipoint image obtained by the wavefront sensor.

FIG. 19 is a view showing an example of a multipoint image obtained by the wavefront sensor 11. A plurality of point images are observed in the range of an optical image to enter the wavefront sensor 11. These point images are images due to light condensed by the plurality of lenses 114 of the lens array 110, and positional deviations of these point images from the reference positions represent phase gradients at those positions. In addition, substantially at a center portion of the wavefront sensor 11, a loss of a point image is observed. This loss is due to the influence of a singularity. That is, at a center point of the singularity, the light intensity is zero, and the phase value is uncertain. Further, there is formed a spiral phase distribution around the center point. These characteristics are considered to have caused such a loss of a point image.

Figure 20:
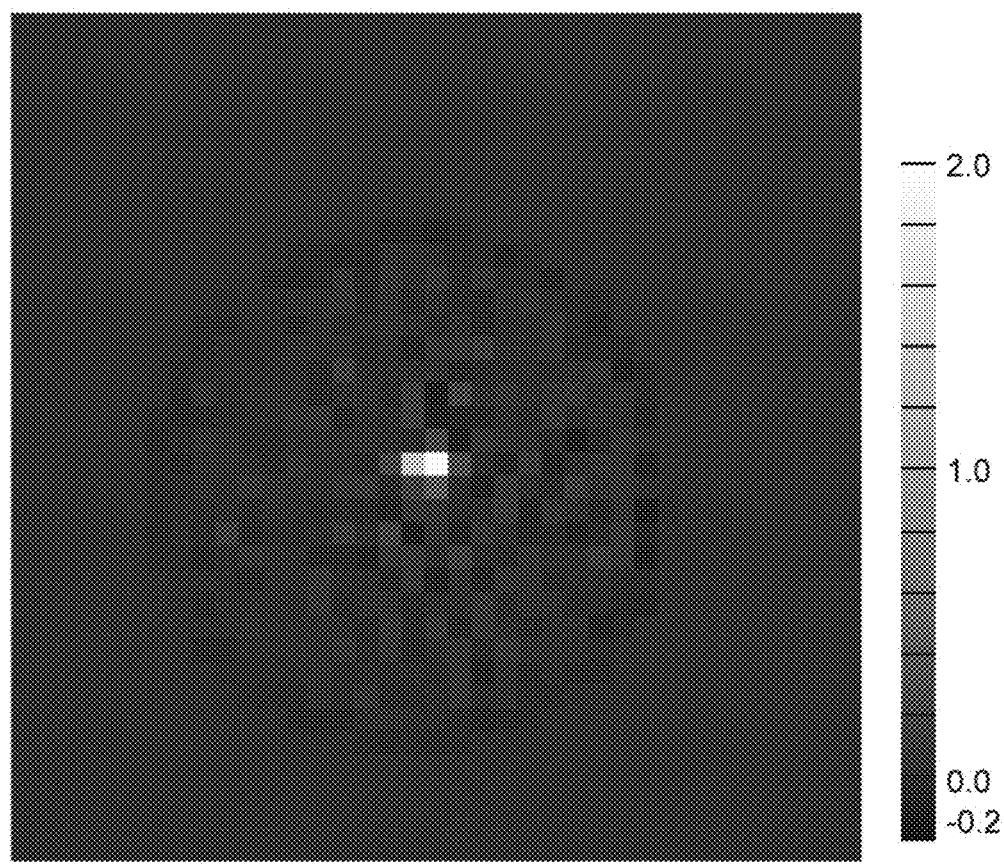
FIG. 20 is a view showing a distribution of circulation values of quasi phase gradients calculated from the multipoint image shown in FIG. 19, and shows that the brighter part has a larger circulation value.
Figure 21:
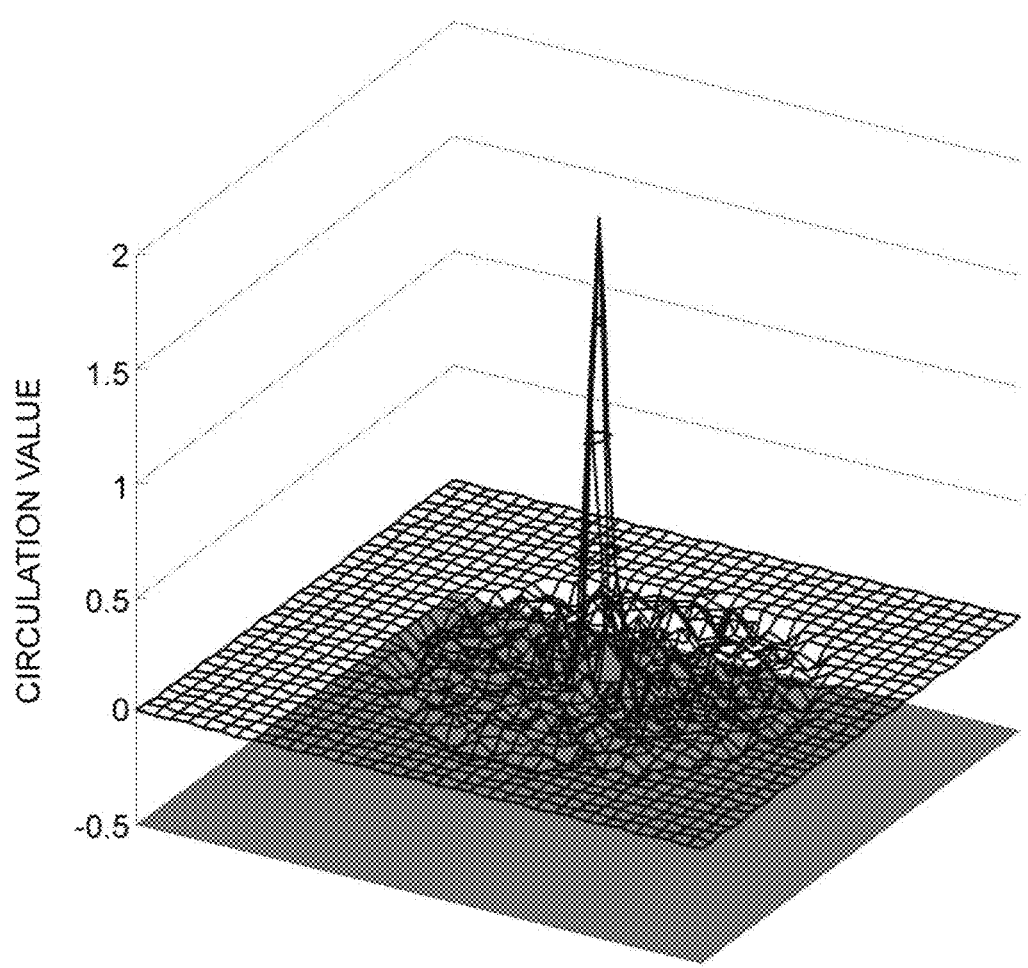
FIG. 21 shows the distribution of circulation values displayed as a three-dimensional graph, in which the axis in the height direction represents the level of the circulation value.

FIG. 20 is a view showing a distribution of circulation values of quasi phase gradients calculated from the multipoint image shown in FIG. 19, and shows that the brighter part has a larger circulation value. As shown in FIG. 20, in this distribution of circulation values, because one peak exists in the vicinity of the center, a singularity exists in the vicinity of the position of this peak. FIG. 21 shows the distribution of circulation values displayed as a three-dimensional graph, in which the axis in the height direction represents the level of the circulation value. In this example, the peak position where the circulation value is maximized is the (18, 19)-th intersection. Further, as a result of a centroid calculation of 3 rows and 3 columns performed at the peak position, an obtained centroid position is (−0.366, 0.146). Because the wavefront sensor 11 used for the experiment has a lens pitch of 280 μm and the image sensor 112 has a pixel pitch of 20 μm, the position of this singularity is (246.88, 268.04) in terms of the coordinates on the detection plane of the wavefront sensor 11. Here, the conversion formula is (18−0.366)×280/20=246.88, (19+0.146)×280/20=268.04.

Figure 22:
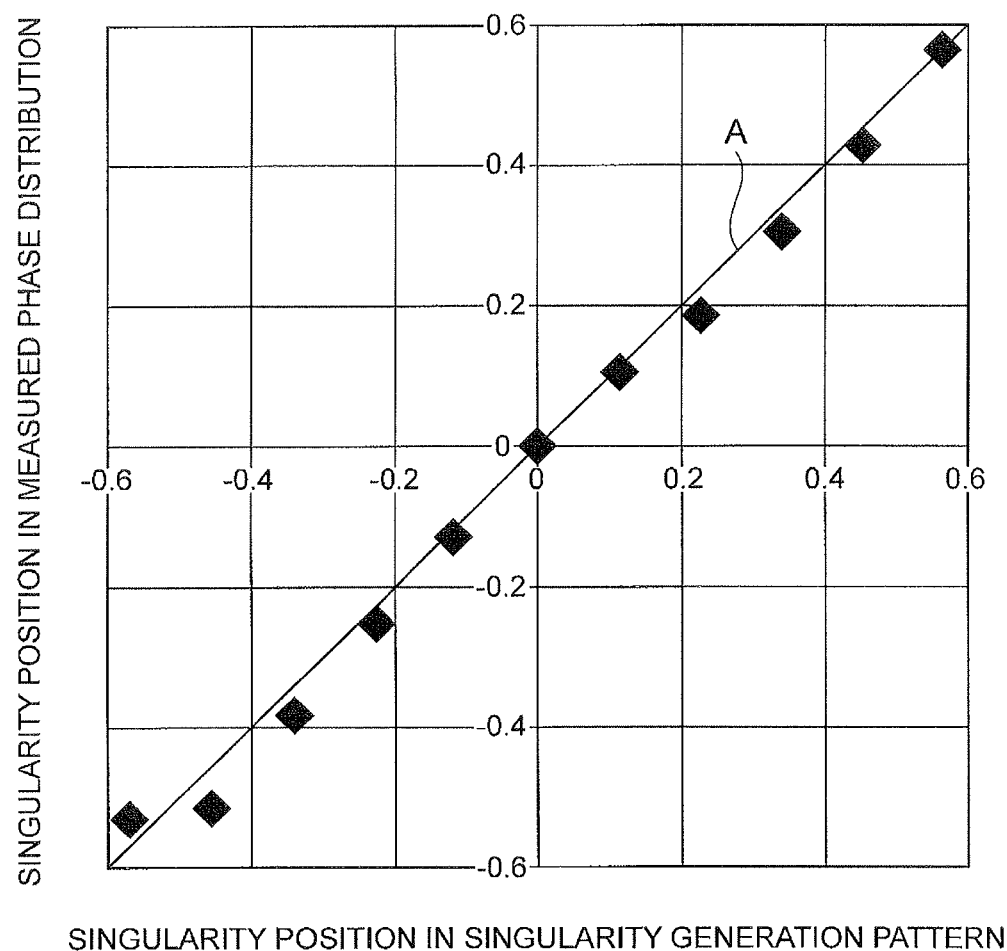
FIG. 22 is a graph showing a relationship of deviation of a measured singularity position and the center movement amount of a singularity generation pattern that is being displayed on the wavefront modulator.

Subsequently, the center of a singularity generation pattern that the wavefront modulator 12 is caused to display is moved one pixel by one pixel, while a multipoint image is taken a plurality of times in the wavefront sensor 11, and a singularity position is calculated. FIG. 22 is a graph showing a relationship of deviation of a measured singularity position and a center movement amount of a singularity generation pattern that is being displayed on the wavefront modulator 12. In addition, the horizontal axis represents the singularity position in the singularity generation pattern, the vertical axis represents the singularity position in a phase distribution measured, and the unit of the vertical and horizontal axes is the lens pitch of the lens array 110 of the wavefront sensor 11. Further, the plotting in the figure represents measurement values, and straight line A represents theoretical values.

As is obvious from FIG. 22, the amount of a positional deviation of the singularity measured in the present experiment resulted approximately equal to the center movement amount of the singularity generation pattern. Further, the maximum value of an error of the measurement value and theoretical value is 0.06, and the RMS value of errors is 0.03, and it is thus confirmed that this method for adjusting the adaptive optics system has a high position measurement accuracy.

An adaptive optics system and a method for adjusting the same according to the present invention are not limited to the embodiment and modified examples described above, and various other modifications can be made. For example, in the above-described embodiment, a phase pattern including a singularity is exemplified as a singularity generation pattern that the wavefront modulator is caused to display, and circulation values are calculated from phase gradients detected in the wavefront sensor to detect a singularity position, however, an adaptive optics system and a method for adjusting the same to which the present invention is applied are not limited to such a phase modulation type. The present invention can also be applied to, for example, a non-phase modulation type (typically, amplitude modulation type) of adaptive optics system or an adaptive optics system of a type to modulate both of the phase and amplitude. Here, in that case, it suffices for the control section to cause the wavefront modulator to display an amplitude pattern including a phase singularity at a predetermined position as a singularity generation pattern, detect a position of the phase singularity in a distribution of the phase and amplitude when, of an optical image modulated by the singularity generation pattern, for example, a first-order diffracted optical image enters the wavefront sensor based on a measurement result in the wavefront sensor, and adjust a positional deviation between an amplitude distribution that is measured in the wavefront sensor and an amplitude pattern for compensation that is displayed on the wavefront modulator based on a positional deviation of the position of the phase singularity with respect to the predetermined position.

Also, an adjustment method of the present invention is not limited to such an adaptive optics system as above for which a wavefront sensor is always arranged at a position to receive an optical image that exits from a wavefront modulator. The present invention can also be applied to, for example, an adaptive optics system that is open-loop controlled or an adaptive optics system without a wavefront sensor. The adaptive optics system that is open-loop controlled is, for example, an adaptive optics system having a configuration in which an optical image from a light source or an observation object is split into two optical images by a beam splitter before entering the wavefront modulator, and one enters the wavefront modulator and the other enters the wavefront sensor. Here, in that case, the above-described wavefront sensor or another wavefront sensor may be temporarily arranged at a conjugate plane of the modulation plane of the wavefront modulator receiving an optical image from the wavefront modulator so as to adjust the position of the wavefront modulator to a desired position by the adjustment method of the present invention.

Further, singularity generation patterns to be used in the present invention include various patterns, besides the pattern shown in FIG. 18. FIG. 23 to FIG. 28 are views showing other examples of the singularity generation pattern. Here, in FIG. 23 to FIG. 28, similar to FIG. 18, the level of the phase of a singularity generation pattern is shown by tones, and the phase of the darkest part is 0 (rad), and the phase of the brightest part is 2π (rad). Further, the boundary of the dark color and bright color is a part where the phase changes from 2π (rad) to 0 (rad), and the phase in that part is continuous in actuality.

Figure 23:
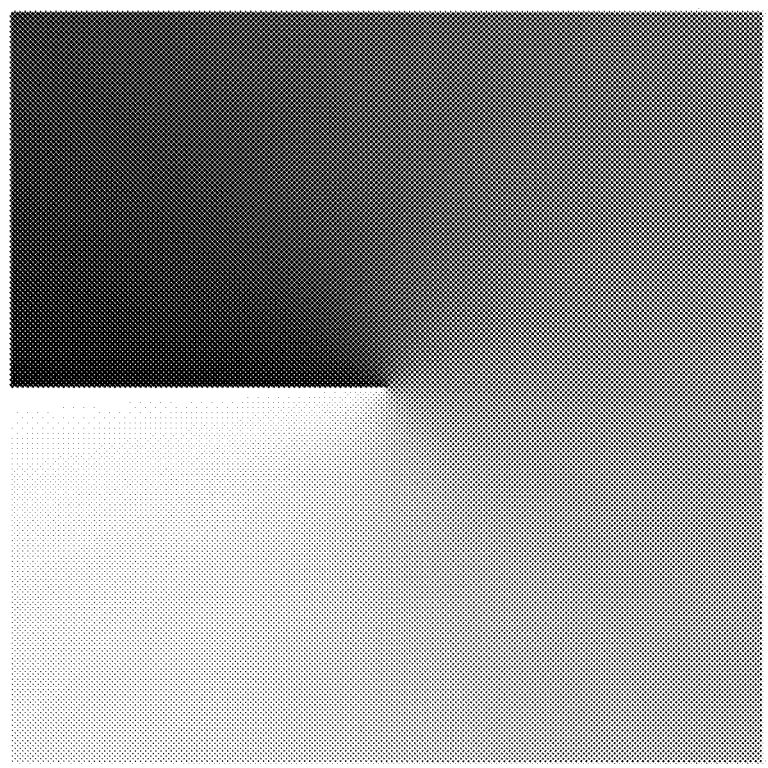
FIG. 23 is a view showing another example of the singularity generation pattern.

The singularity generation pattern shown in FIG. 23 has a clockwise spiral phase distribution, and has one boundary in one round, so that the topological charge of this singularity generation pattern is 1. Moreover, a center part of the spiral corresponds to a singularity.

Figure 24:
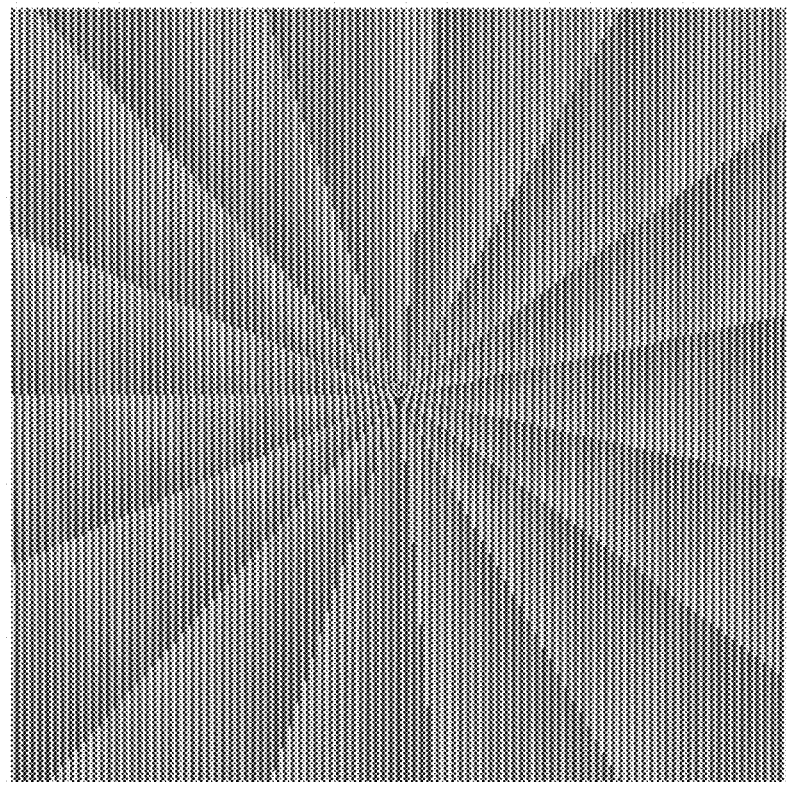
FIG. 24 is a view showing another example of the singularity generation pattern.

Also, FIG. 24 shows an example in which a blazed phase grating is added to the spiral phase distribution shown in FIG. 18. In this example, a center part of the spiral corresponds to a singularity.

Figure 25:
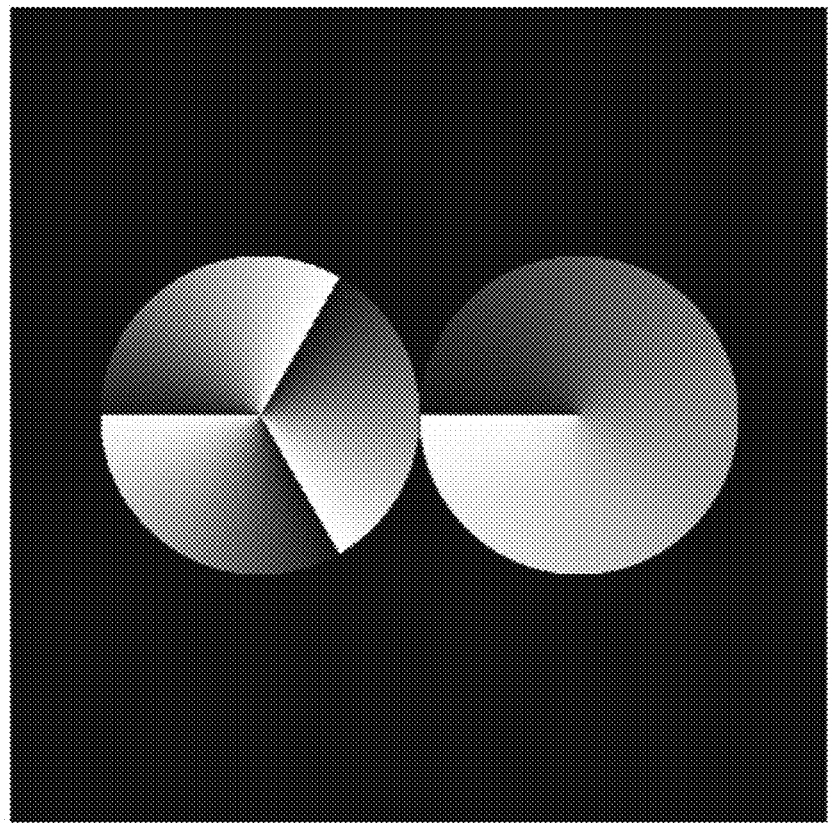
FIG. 25 is a view showing another example of the singularity generation pattern.
Figure 26:
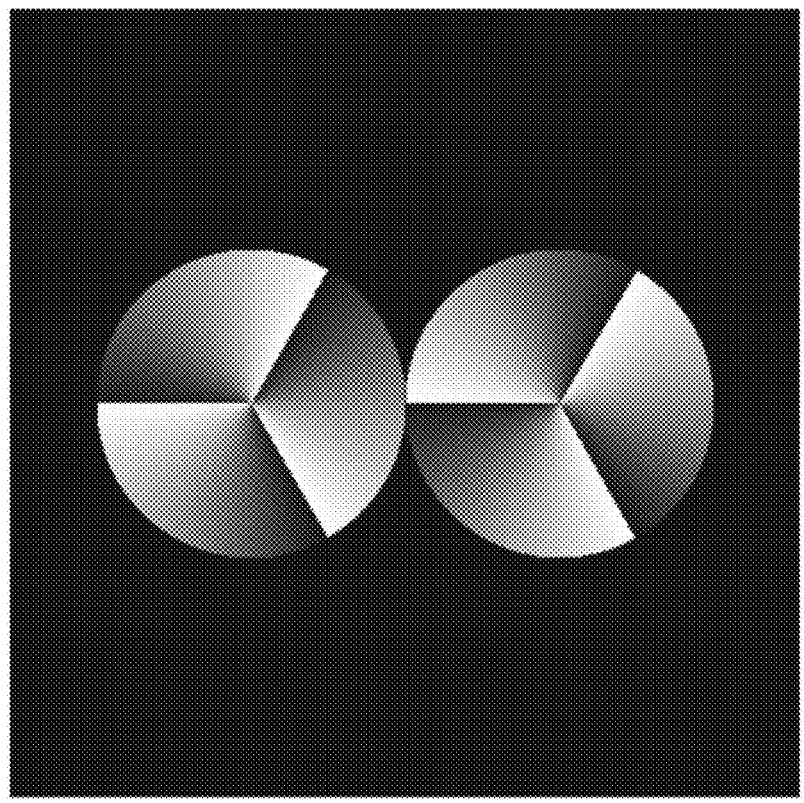
FIG. 26 is a view showing another example of the singularity generation pattern.

Also, FIG. 25 and FIG. 26 are views each showing a singularity generation pattern having two singularities. The singularity generation pattern shown in FIG. 25 has a clockwise spiral phase distribution (left side) the topological charge of which is 3 and a clockwise spiral phase distribution (right side) the topological charge of which is 1. Further, the singularity generation pattern shown in FIG. 26 has a clockwise spiral phase distribution (left side) the topological charge of which is 3 and a counterclockwise spiral phase distribution (right side) the topological charge of which is 3.

Figure 27:
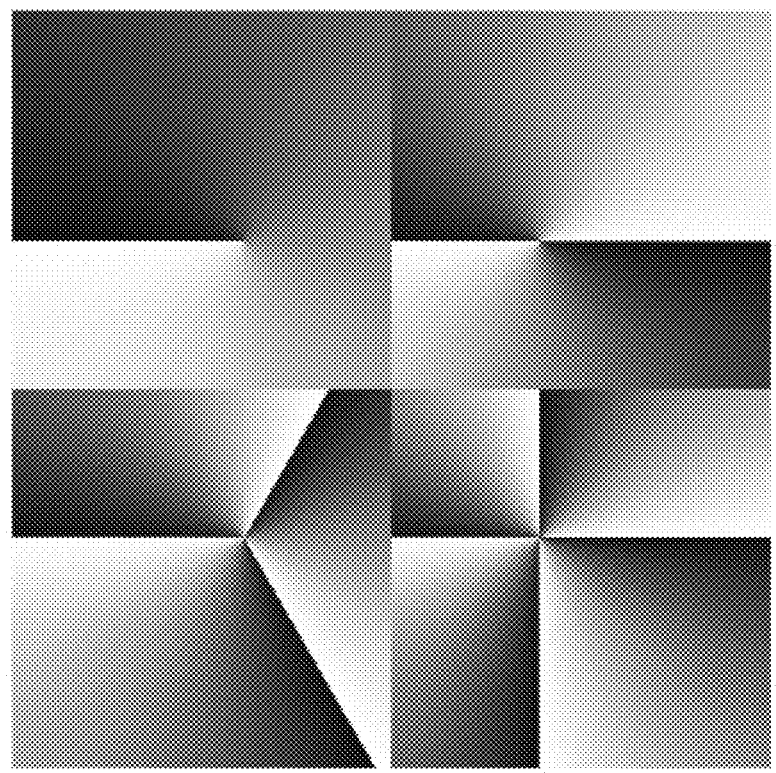
FIG. 27 is a view showing another example of the singularity generation pattern.
Figure 28:
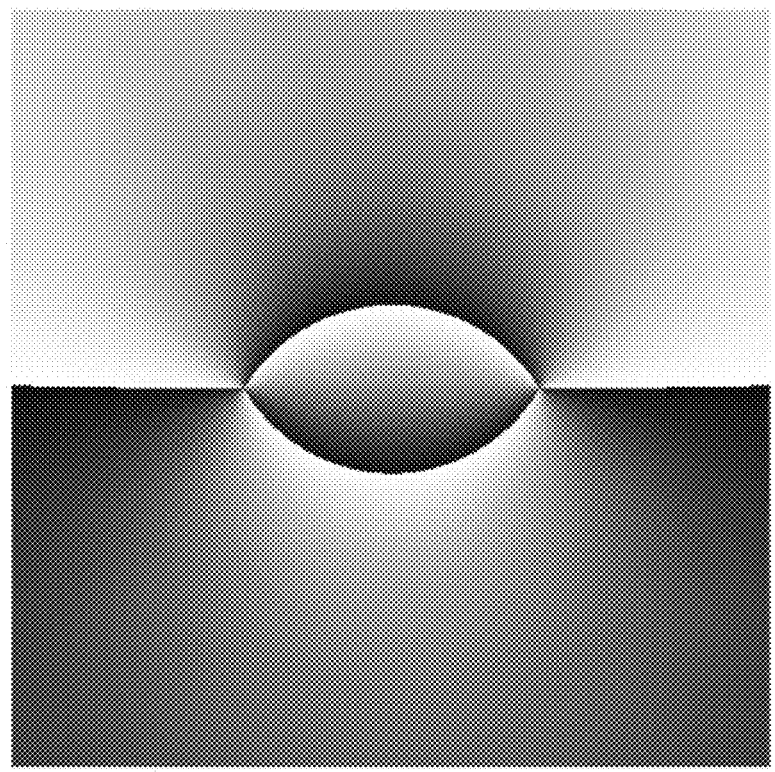
FIG. 28 is a view showing another example of the singularity generation pattern.

Also, the singularity generation pattern shown in FIG. 27 is divided into four regions, and singularities are included one each in the respective regions. Also, the singularity generation pattern shown in FIG. 28 is an example of a singularity generation pattern prepared by superimposing two spiral phase distributions having different center points over the entire region. The singularity generation pattern shown in FIG. 28 includes two singularities that are separated to left and right.

Further, similar to FIG. 24, a blazed phase grating may be added to the singularity generation patterns shown in FIG. 25 to FIG. 28.

Further, in the above-described embodiment, a non-interference type of Shack-Hartmann type wavefront sensor is used as the wavefront sensor, but in an adaptive optics system and a method for adjusting the same according to the present invention, another non-interference type wavefront sensor or an interference type wavefront sensor (such as, for example, a curvature sensor or shearing interferometer) may be used.

A method for adjusting an adaptive optics system according to the above-described embodiment is a method for adjusting an adaptive optics system which includes a wavefront modulator that receives an optical image from a light source or an observation object, and a wavefront sensor that receives an optical image from the wavefront modulator to measure a wavefront shape of the optical image, and compensates for a wavefront distortion by controlling a pattern to be displayed on the wavefront modulator based on the wavefront shape measured by the wavefront sensor, and is configured to include a first step of causing the wavefront modulator to display a singularity generation pattern which is a pattern including a phase singularity (hereinafter, "phase singularity" is abbreviated as "singularity") at a predetermined position, a second step of measuring in the wavefront sensor a wavefront shape for adjustment which is a wavefront shape when an optical image modulated by the singularity generation pattern enters the wavefront sensor, a third step of detecting a position of the singularity in the adjustment wavefront shape from a measurement result in the wavefront sensor, and a fourth step of adjusting a positional deviation between a wavefront shape being measured in the wavefront sensor and a pattern for compensation being displayed on the wavefront modulator based on a positional deviation of the position of the singularity detected in the third step from the predetermined position.

Also, the method for adjusting an adaptive optics system may be configured such that, in the third step, in the adjustment wavefront shape, a closed-path integration value of a phase gradient is calculated for each of the unit regions composing the wavefront sensor, and a position of the unit region where the closed-path integration value peaks (hereinafter, referred to as a peak position) is determined to detect the position of the singularity assuming that the singularity is included in the unit region of the peak position.

Also, the method for adjusting an adaptive optics system may be configured such that the position of the singularity within the unit region of the peak position is calculated based on the closed-path integration values of the unit regions located around the peak position.

Also, the method for adjusting an adaptive optics system may be configured such that the wavefront sensor is a Shack-Hartmann type wavefront sensor.

Also, the method for adjusting an adaptive optics system may be configured such that the singularity generation pattern has a spiral wavefront shape.

An adaptive optics system according to the above-described embodiment is configured to include a wavefront modulator that receives an optical image from a light source or an observation object, and a wavefront sensor that receives an optical image from the wavefront modulator to measure a wavefront shape of the optical image, and a control section that compensates for a wavefront distortion by controlling a pattern to be displayed on the wavefront modulator based on the wavefront shape measured by the wavefront sensor, and in the system, the control section includes a singularity generation pattern preparing section that causes the wavefront modulator to display a singularity generation pattern which is a pattern including a singular point at a predetermined position, and a singularity detecting section that detects a position of the singular point in a wavefront shape for adjustment which is a wavefront shape when an optical image modulated by the singularity generation pattern entered the wavefront sensor, based on a measurement result in the wavefront sensor, and the control section adjusts a positional deviation between a wavefront shape being measured in the wavefront sensor and a pattern for compensation being displayed on the wavefront modulator based on a positional deviation of the position of the singularity detected by the singularity detecting section from the predetermined position.

Also, the adaptive optics system may be configured such that the singularity detecting section, in the adjustment wavefront shape, calculates a closed-path integration value of a phase gradient for each of the unit regions composing the wavefront sensor, and determines a position of the unit region where the closed-path integration value peaks (hereinafter, referred to as a peak position) to detect the position of the singularity assuming that the singularity is included in the unit region of the peak position.

Also, the adaptive optics system may be configured such that the singularity detecting section calculates the position of the singularity within the unit region of the peak position based on the closed-path integration values of the unit regions located around the peak position.

Also, the adaptive optics system may be configured such that the wavefront sensor is a Shack-Hartmann type wavefront sensor.

Also, the adaptive optics system may be configured such that the singularity generation pattern has a spiral wavefront shape.

INDUSTRIAL APPLICABILITY

The present invention can be applied as a method for adjusting an adaptive optics system and an adaptive optics system capable of correcting a positional deviation between a phase distribution measured in a wavefront sensor and a compensation phase pattern displayed on a wavefront modulator in a short time and with high accuracy.

REFERENCE SIGNS LIST 10A, 10B, 10C—adaptive optics system, 11—wavefront sensor, 12—wavefront modulator, 13A, 13B, 13C—control section, 14—beam splitter, 101—singularity generation pattern preparing section, 102—singularity detecting section, S—singularity, S1—measurement signal, S2, S3, S4—control signal.

The invention claimed is:
1. A method for adjusting an adaptive optics system which includes a wavefront modulator receiving an optical image from a light source or an observation object, and a wavefront sensor receiving an optical image from the wavefront modulator to measure a wavefront shape of the optical image, and compensates for a wavefront distortion by controlling a pattern to be displayed on the wavefront modulator based on the wavefront shape measured by the wavefront sensor, comprising:

a first step of causing the wavefront modulator to display a singularity generation pattern which is a pattern including a singularity at a predetermined position;
a second step of measuring in the wavefront sensor an adjustment wavefront shape which is a wavefront shape when an optical image modulated by the singularity generation pattern enters the wavefront sensor;
a third step of detecting a position of the singularity in the adjustment wavefront shape from a measurement result in the wavefront sensor; and
a fourth step of adjusting a positional deviation between a wavefront shape measured in the wavefront sensor and a compensation pattern displayed on the wavefront modulator based on a positional deviation of the position of the singularity detected in the third step with respect to the predetermined position.

2. The method for adjusting an adaptive optics system according to claim 1, wherein, in the third step, in the adjustment wavefront shape, a closed-path integration value of a phase gradient is calculated for each of the unit regions composing the wavefront sensor, and a position of the unit region where the closed-path integration value peaks (hereinafter, referred to as a peak position) is determined to detect the position of the singularity assuming that the singularity is included in the unit region of the peak position.

3. The method for adjusting an adaptive optics system according to claim 2, wherein the position of the singularity within the unit region of the peak position is calculated based on the closed-path integration values of the unit regions located around the peak position.

4. The method for adjusting an adaptive optics system according to claim 1, wherein the wavefront sensor is a Shack-Hartmann type wavefront sensor.

5. The method for adjusting an adaptive optics system according to claim 1, wherein the singularity generation pattern has a spiral wavefront shape.

6. An adaptive optics system comprising:
a wavefront modulator receiving an optical image from a light source or an observation object;
a wavefront sensor receiving an optical image from the wavefront modulator to measure a wavefront shape of the optical image; and
a control section compensating for a wavefront distortion by controlling a pattern to be displayed on the wavefront modulator based on the wavefront shape measured by the wavefront sensor, wherein
the control section includes:
a singularity generation pattern preparing section causing the wavefront modulator to
display a singularity generation pattern which is a pattern including a singularity at a predetermined position; and
a singularity detecting section detecting a position of the singularity in an adjustment wavefront shape which is a wavefront shape when an optical image modulated by the singularity generation pattern enters the wavefront sensor, based on a measurement result in the wavefront sensor, and
the control section adjusts a positional deviation between a wavefront shape measured in the wavefront sensor and a compensation pattern displayed on the wavefront modulator based on a positional deviation of the position of the singularity detected by the singularity detecting section with respect to the predetermined position.

7. The adaptive optics system according to claim 6, wherein the singularity detecting section, in the adjustment wavefront shape, calculates a closed-path integration value of a phase gradient for each of the unit regions composing the wavefront sensor, and determines a position of the unit region where the closed-path integration value peaks (hereinafter, referred to as a peak position) to detect the position of the singularity assuming that the singularity is included in the unit region of the peak position.

8. The adaptive optics system according to claim 7, wherein the singularity detecting section calculates the position of the singularity within the unit region of the peak position based on the closed-path integration values of the unit regions located around the peak position.

9. The adaptive optics system according to claim 6, wherein the wavefront sensor is a Shack-Hartmann type wavefront sensor.

10. The adaptive optics system according to claim 6, wherein the singularity generation pattern has a spiral wavefront shape.

* * * * *